US009857351B2

(12) United States Patent
Saleem

(10) Patent No.: US 9,857,351 B2
(45) Date of Patent: Jan. 2, 2018

(54) CONCRETE REINFORCEMENT ASSEMBLY, METHOD OF INSTALLATION, AND METHOD TO DETERMINE CYCLIC LOAD RESPONSE

(71) Applicant: University of Dammam, Dammam (SA)

(72) Inventor: Muhammad Saleem, Dammam (SA)

(73) Assignee: University of Dammam, Dammam (SA)

( * ) Notice: Subject to any disclaimer, the term of this patent is extended or adjusted under 35 U.S.C. 154(b) by 183 days.

(21) Appl. No.: 15/040,400

(22) Filed: Feb. 10, 2016

(65) Prior Publication Data
US 2017/0131259 A1    May 11, 2017

Related U.S. Application Data

(60) Provisional application No. 62/252,911, filed on Nov. 9, 2015.

(51) Int. Cl.
*G01N 3/00*    (2006.01)
*G01N 19/00*    (2006.01)
(Continued)

(52) U.S. Cl.
CPC ........... *G01N 33/383* (2013.01); *E04C 5/125* (2013.01); *E04G 23/0218* (2013.01);
(Continued)

(58) Field of Classification Search
None
See application file for complete search history.

(56) References Cited

U.S. PATENT DOCUMENTS 7,426,807 B2 *  9/2008  Cadwell .................... E04C 3/34
                                        52/834
7,682,993 B2 *  3/2010  Derrigan ................. B32B 5/024
                                        442/136
(Continued)

FOREIGN PATENT DOCUMENTS

JP    2000-314174 A    11/2000
JP    2009-203716 A     9/2009
(Continued)

*Primary Examiner* — Peter Macchiarolo
*Assistant Examiner* — Jermaine Jenkins
(74) *Attorney, Agent, or Firm* — Oblon, McClelland, Maier & Neustadt, L.L.P.

(57) ABSTRACT

A concrete reinforcement assembly including a first hollow metal sleeve, an anchor bar that is nested concentrically within the first hollow metal sleeve, and a second hollow metal sleeve. The first hollow metal sleeve is nested concentrically within the second hollow metal sleeve and an infill material is disposed in between the first hollow metal sleeve and the anchor bar, and in between the first hollow metal sleeve and the second hollow metal sleeve. The infill material dampens energy transfer to and from the concrete reinforcement assembly when employed for structural stability in a concrete structure. A method for repairing a damaged concrete anchor with the concrete reinforcement assembly. A non-transitory computer readable medium having stored thereon a program that, when executed by a computer, causes the computer to execute a method of determining a cyclic response factor of a concrete reinforcement assembly in a concrete structure.

20 Claims, 21 Drawing Sheets

(51) Int. Cl.
*E04C 3/00* (2006.01)
*E04C 5/08* (2006.01)
*G01N 33/38* (2006.01)
*E04C 5/12* (2006.01)
*G01N 3/24* (2006.01)
*E04H 9/02* (2006.01)
*E04G 23/02* (2006.01)

(52) U.S. Cl.
CPC .............. *E04H 9/021* (2013.01); *G01N 3/24* (2013.01); *G01N 2203/0025* (2013.01)

(56) References Cited

U.S. PATENT DOCUMENTS

| | | | | |
|---|---|---|---|---|
| 8,104,242 | B1* | 1/2012 | Fouad | E04C 3/34 |
| | | | | 52/223.14 |
| 8,281,545 | B2* | 10/2012 | Choi | E04C 3/34 |
| | | | | 52/745.04 |
| 9,546,490 | B2* | 1/2017 | Kraus | E04G 23/0218 |
| 9,637,923 | B2* | 5/2017 | Radhouane | E04C 3/34 |
| 2012/0066994 | A1* | 3/2012 | Gibson | B29C 70/52 |
| | | | | 52/309.13 |
| 2016/0251865 | A1* | 9/2016 | Martina | E04G 23/0218 |
| | | | | 52/223.4 |
| 2017/0254083 | A1* | 9/2017 | Wu | C04B 18/16 |

FOREIGN PATENT DOCUMENTS

| | | |
|---|---|---|
| JP | 4844926 62 | 12/2011 |
| JP | 5616625 B2 | 10/2014 |

* cited by examiner

| 201 | $\dfrac{q_{\tau 1}}{q_{y1}} = \dfrac{q_{\tau 2}}{q_{y2}}$ | De-bonding extension criterion |
|---|---|---|
| 202 | $\dfrac{q_{\tau 1}}{q_{y1}} > \dfrac{q_{\tau 2}}{q_{y2}}$ | De-bonding extension criterion |
| 203 | $\dfrac{q_{\tau 1}}{q_{y1}} < \dfrac{q_{\tau 2}}{q_{y2}}$ | De-bonding extension criterion |
| 204 | $q_{fco}, q_{fcr}, q_{fto}, q_{ft1}$ | Frictional shear stress parameters |
| 205 | $P, P^*$ | Shear stress, Shear stress factor |
| 206 | $U, U^*$ | Shear slip, Shear slip factor |
| 207 | $k_x$ | Stiffness coefficient, 'x' subscript denotes different stiffness coefficients (e.g. $k_e, k_{imb}, k_{rec}, k_{enb}, k_{dt}$) |
| 208 | $\alpha, \beta$ | Stability coefficients |
| 209 | $\gamma, \lambda, \varsigma, \kappa, \xi, \iota$ | Control coefficients obtained by trial and error |

FIG. 2

| | |
|---|---|
| 401 | $P^* = k_{ini} U^*, U^* = \dfrac{q_{yi}}{k_{ini}}, q_f = 0, k_{ini} = k_e$ |
| 402 | $P^* = U^*(1-\lambda\alpha)k_{dt}, \quad U^* = \text{given}, k_{dt} = \gamma k_{ini}$ |
| 403 | $P^* = 0, \quad U^* = U - (1+\alpha)\left(\dfrac{U(1-\lambda\alpha)k_{dt}}{\beta}\right)k_{rec}, \quad k_{rec} = k_e - k_{dt}$ |
| 404 | $P^* = -(1-\lambda\alpha)[U^*(1-\lambda\alpha)k_{dt}], \quad U^* = U - (1+\alpha)\left(\dfrac{U(1-\lambda\alpha)}{\varsigma\beta k_{rec}}k_{dt}\right)$ |
| 405 | $P^* = P, \quad U^* = 0$ |
| 406 | $P'^* = -\alpha k_{dc} U, \quad U'^* = 0, k_{dc} = k_{dt}$ |

*FIG. 4*

| | |
|---|---|
| 601 | $P^* = \beta P_{peak}, \; U^* = \beta U_{peak}$ |
| 602 | $P^* = (1-\lambda\alpha)k_{dt}U, \; U^* = \text{given}, \; k_{dt} = \gamma k_{ini}$ |
| 603 | $P^* = 0, \; U^* = U - (1+\alpha)(1-\lambda\alpha)\left(\frac{k_{dt}}{\beta k_{rec}}\right)U, \; k_{rec} = k_e - k_{dt}$ |
| 604 | $P^* = -(1+\alpha)(1-\lambda\alpha)k_{dt}U, \; U^* = U - (1+\alpha)(\frac{Uk_{dt}(1-\lambda\alpha)}{\kappa\beta k_{rec}}), k_{rec} = k_e - k_{dt}$ |
| 605 | $P^* = P, \; U^* = 0$ |
| 606 | $P^* = -(\alpha - \xi)k_{dc}U, \; U^* = -\alpha U$ |
| 607 | $P^* = (1+\alpha)P', \; U^* = -(\alpha + \iota)U$ |
| 608 | $P^* = -\left(1 - \frac{\alpha}{\gamma}\right)P, \; U^* = U^* + (1-\lambda\alpha)k_{dt}U/k_{dc}$ |
| 609 | $P^* = P + \lambda\alpha P, \; U^* = 0$ |

FIG. 6

CONCRETE REINFORCEMENT ASSEMBLY, METHOD OF INSTALLATION, AND METHOD TO DETERMINE CYCLIC LOAD RESPONSE

CROSS REFERENCE TO RELATED APPLICATIONS

This application claims the benefit of U.S. Provisional Application No. 62/252,911 filed Nov. 9, 2015.

BACKGROUND OF THE INVENTION

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Post-installed anchor bars are widely employed in the retrofitting industry to strengthen reinforced concrete structures. The purpose of post-installed anchor bars is to improve the flexure and shear capacity of the concrete structures. Many techniques employ post-installed anchor bars for the retrofitting process and among them, the most common is the technique of concrete jacketing. See Ishibashi, T.; Tsukishima, D.: Seismic damage of and seismic rehabilitation techniques for railway reinforced concrete structures. J. Adv. Concr. Technol. 7(3), 287-296 (2009); Ishibashi, T.; Tsuyoshi, T.; Kobayashi, K.: Seismic retrofitting methods newly developed for railway concrete structures. J. Adv. Concr. Technol. 2, 65-76 (2004), each incorporated herein in its entirety.

Traditionally, the anchor bar is commonly attached to the structural member by drilling a hole and injecting infill material, commonly an epoxy resin, to hold the anchor bar in place. However, very little attention in the past has been focused on the anchor-infill assembly structure, which can be modified to control the deformational response of the post-installed anchor bar.

Structures are often under the stress of environmental conditions such as storm waves and earthquakes, both of which can cause a cyclic motion of the anchor-infill assembly. The cyclic motion and resulting effect on the anchor-infill assembly structure is called a cyclic pull-out push-in response. Pull-out is the motion of the anchor bar moving out of the anchor-infill assembly and push-in is the motion of the anchor bar moving into the anchor-infill assembly. As a result of the pull-out, push-in sequence the anchor bar and the anchor-infill assembly has a variety of shear forces exerted upon it that may result in expanding cracks in the surrounding concrete structure. For the purpose of simulating the cyclic pull-out push-in response of the post-installed anchor bar, a piecewise linear cyclic shear-lag material model can represent the local bond behavior of the infill material, thus testing the infill material's resilience, strength, and durability. Shear lag describes behavior at an end connection of a tension member where some but not all of the cross-sectional elements are connected. An example of shear lag can be the shear stress observed on an outer surface of an end of a piston shaft that is partially remaining in a cylinder during an upward stroke.

The cyclic response of the post-installed anchor bar can be divided into two categories, namely one with indentation and one without indentation, where indentation represents the concrete crushing at the base of the drilled hole used for installing post-installed anchor bar and slight buckling of the post-installed anchor bar at the top of anchor hole under push-in motion. The effect of interface de-bonding, or cracking, on a stiffness value of an infill material can be incorporated in the form of stiffness deterioration value, and the lateral pressure and Poisson's effect can be incorporated in a form of a stiffness recovery value accompanied with increased constant frictional shear strength. The Poisson's effect is the name given to the observation of a material being compressed in one direction, leading to an expansion of the material in the other two directions perpendicular to the direction of compression.

In view of the forgoing, one objective of the present invention is to provide a concrete reinforcement assembly, a method of installation of the concrete reinforcement assembly and a non-transitory computer readable medium having stored thereon a program that, when executed by a computer, causes the computer to carry out a method of determining a cyclic response factor of a concrete reinforcement assembly.

BRIEF SUMMARY OF THE INVENTION

According to a first aspect the disclosure is directed to a concrete reinforcement assembly having a first hollow metal sleeve having two ends, an anchor bar that is nested concentrically within the first hollow metal sleeve and is moveable along a longitudinal axis of the first hollow metal sleeve. The assembly includes a second hollow metal sleeve having two ends, in which the first hollow metal sleeve is nested concentrically. The assembly further includes an infill material that is disposed in between the first hollow metal sleeve and the anchor bar, in between the first hollow metal sleeve and the second hollow metal sleeve and cured in place and is meant to dampen energy transfer to and from the concrete reinforcement assembly dampen energy transfer to and from the concrete reinforcement assembly. The first hollow metal sleeve and second hollow metal sleeve are no longer hollow once the infill material is disposed inside the assembly and the assembly is placed inside a hollow cavity in a concrete structure. The concrete reinforcement assembly is equipped to be inserted into the hollow cavity in a concrete structure and adapted to structurally reinforce the concrete structure.

Some embodiments of the concrete reinforcement assembly include the anchor bar having an end adapted to manual hammering or neumatic hammering, or the like, which may occur during installation of the concrete reinforcement assembly.

Some embodiments may include the concrete reinforcement assembly further having a plurality of mechanical anchors attached to an outer surface of the second hollow metal sleeve adapted to secure the concrete reinforcement assembly to the hollow cavity in the concrete structure by opening outwardly from the outer surface.

Some embodiments may include the concrete reinforcement assembly having the mechanical anchors attached to the outer surface of the second hollow metal sleeve by a hinge and the mechanical anchors can adopt an open position or closed position, where the mechanical anchors extend outwardly when in the open position.

Some embodiments may include the concrete reinforcement assembly in which the mechanical anchors are in an open position when the anchor bar is within the concrete reinforcement assembly.

Some embodiments may include the concrete reinforcement assembly having mechanical anchors comprising steel.

Some embodiments may include the concrete reinforcement assembly having mechanical anchors that are attached to the outer surface of the second hollow metal sleeve at a variety of horizontally and vertically separated levels.

Some embodiments may include the concrete reinforcement assembly having infill material comprising (a) at least one reinforcing material selected from the group consisting of an elastomeric polymer, a glass fiber epoxy composite, a carbon nanotube epoxy composite, and an epoxy and (b) at least one anti-corrosive additive selected from the group consisting of a polythiophene, calcium sulfonate, barium sulfonate, and an amine.

Some embodiments may include the concrete reinforcement assembly in which an elastic modulus ratio of the anchor bar to the infill material is 8-25.

Some embodiments may include the concrete reinforcement assembly in which the first hollow metal sleeve, second hollow metal sleeve, and the anchor bar comprise carbon steel or alloy steel.

Some embodiments may include the concrete reinforcement assembly in which a longitudinal length of the first hollow metal sleeve and the second hollow metal sleeve is the same as a longitudinal length of the hollow cavity.

Some embodiments may include the concrete reinforcement assembly in which a ratio of a longest cross sectional length of the anchor bar to a longitudinal length of the hollow cavity ranges from 1:20-1:50.

Some embodiments may include the concrete reinforcement assembly in which the anchor bar is at least 5%-50% longer in length than the hollow cavity.

Some embodiments may include the concrete reinforcement assembly in which a cross section of the anchor bar has a shape similar to a cross section of the first hollow metal sleeve.

Some embodiments may include the concrete reinforcement assembly in which the anchor bar, the first hollow metal sleeve, and the second hollow metal sleeve are cylindrical.

According to a second aspect, the present disclosure is directed to a method for repairing a damaged concrete anchor including removing the damaged concrete anchor from a hollow cavity in a concrete structure and inserting a concrete reinforcement assembly having a first hollow metal sleeve nested concentrically within a second hollow metal sleeve. The second hollow metal sleeve may have an outer surface attached to a plurality of mechanical anchors by a plurality of hinges. The mechanical anchors are adapted to secure the concrete reinforcement assembly to the hollow cavity in the concrete structure. The method further includes disposing an infill material in between the first hollow metal sleeve and the second hollow metal sleeve, inserting an anchor bar concentrically within the first hollow metal sleeve such that the anchor bar is moveable along a longitudinal axis of the first hollow metal sleeve, and disposing an infill material in between the first hollow metal sleeve and the anchor bar.

In some implementations, the method further includes resurfacing the hollow cavity in the concrete structure after removing the damaged concrete anchor.

In some implementations of the method, the insertion of the anchor bar triggers a plurality of mechanical anchors to open.

According to a third aspect, the present disclosure is directed to a non-transitory computer readable medium having stored thereon a program that, when executed by a computer, causes the computer to carry out a method of determining a cyclic response factor of a concrete reinforcement assembly in a concrete structure including receiving a plurality of parameters of the concrete reinforcement assembly and evaluating the plurality of parameters of the concrete reinforcement assembly, evaluating a de-bonding extension criterion evaluating a first interfacial de-bonding value based on the plurality of parameters of the concrete reinforcement assembly determining a shear stress parameter and a shear slip parameter and determining a plurality of frictional shear stress parameters, estimating a shear stress factor, a shear slip factor, and a stiffness factor, establishing a relationship between the plurality of parameters of the concrete reinforcement assembly, the de-bonding extension criterion, the shear stress parameter, shear slip parameter, and the plurality of frictional shear stress parameters, updating the plurality of parameters of the concrete reinforcement assembly, and obtaining the cyclic response factor.

In some implementations the method further includes evaluating a second interfacial de-bonding based on the plurality of parameters.

In some implementations of the method, the plurality of parameters includes at least one of a geometrical parameter of the concrete reinforcement assembly, an elastic modulus ratio of the concrete reinforcement assembly, and a loading history of the concrete structure.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 2 is an example of a list of criterion and variables employed to determine a cyclic response factor of the concrete reinforcement assembly;

FIG. 4 is an example list of the equations employed in the determination of the cyclic response of the concrete reinforcement assembly;

FIG. 6 is an example list of the equations employed in the determination of the cyclic response of the concrete reinforcement assembly;

DETAILED DESCRIPTION OF THE EMBODIMENTS

Figure 1:
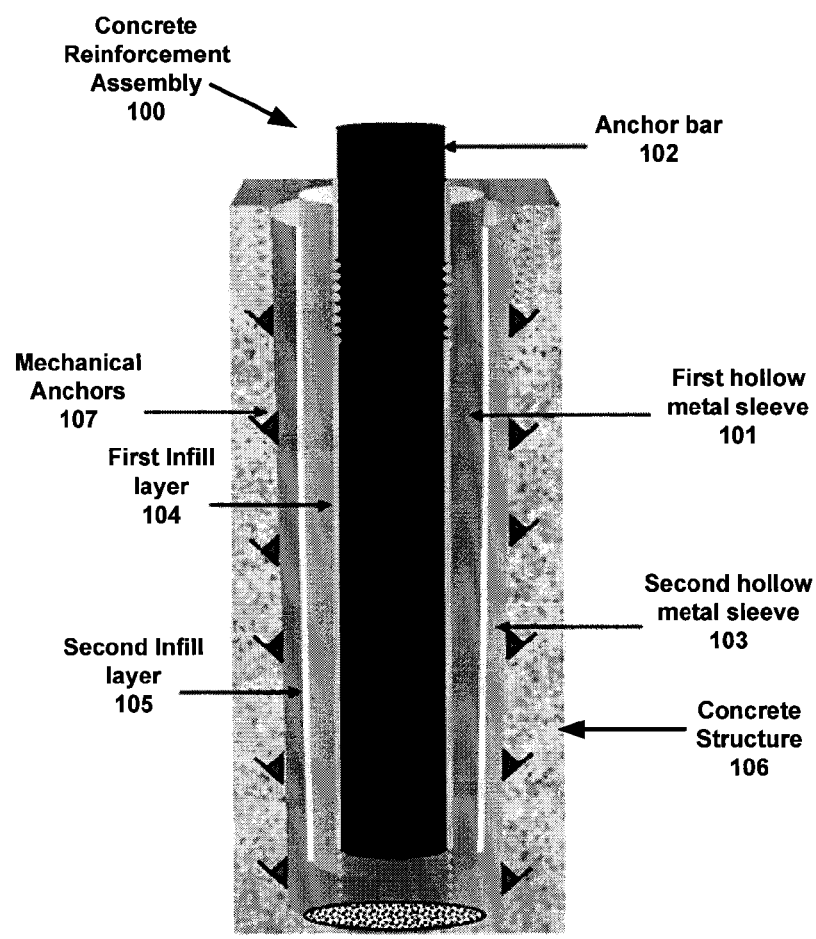
FIG. 1 is an exemplary schematic depiction of a concrete reinforcement assembly.

The present disclosure relates to a concrete reinforcement assembly which results in larger energy absorption capacity during the cyclic response of a post-installed anchor bar. Referring now to the drawings, wherein like reference numerals designate identical or corresponding parts. FIG. 1 depicts an exemplary concrete reinforcement assembly of the present disclosure. The concrete reinforcement assembly 100 has a first hollow metal sleeve 101 having two ends and an anchor bar 102 that is nested concentrically within the first hollow metal sleeve 101. The anchor bar 102 is moveable along a longitudinal axis of the first hollow metal sleeve 101 prior to disposing the infill material and after disposing the infill material, although after disposing the infill material the anchor bar is moveable but inhibited by the infill material. The assembly includes a second hollow metal sleeve 103 having two ends, in which the first hollow metal sleeve 101 is nested concentrically. In some embodiments, the first hollow metal sleeve 101, second hollow metal sleeve 103, and the anchor bar 102 may be comprised of high strength steel or the like to withstand forces applied to the concrete reinforcement assembly 100.

The assembly further includes an infill material that is disposed in between the first hollow metal sleeve 101 and the anchor bar 102, in between the first hollow metal sleeve 101 and the second hollow metal sleeve 103. The infill material is partially liquid when being disposed. However, after curing when the concrete reinforcement assembly is installed, the infill material dampens energy transfer to and from the concrete reinforcement assembly 100. The infill material is divided in two layers, a first infill layer 104 between the anchor bar 102 and the first hollow metal sleeve 101, and a second infill layer 105 between the first hollow metal sleeve 101 and the second hollow metal sleeve 103. The first 104 and second infill layer 105 provide for the added energy absorption capacity of the concrete reinforcement assembly and confine damage caused by the cyclic response of the anchor bar 102 to the assembly 100. Energy absorption capacity may be measured in terms of a thickness of the first infill layer or second infill layer and/or in terms of the a stiffness coefficient of the infill material. The concrete reinforcement assembly 100 is equipped to be inserted into a hollow cavity in a concrete structure 106 to structurally reinforce the concrete structure. The infill material may cure inside the concrete reinforcement assembly after the concrete reinforcement assembly is inserted into a hollow cavity. In some embodiments, the infill material may be partially or fully cured inside the concrete reinforcement assembly, but outside the hollow cavity, and after installation of the concrete reinforcement assembly inside the hollow cavity, the remainder of the infill material may cure completely inside the hollow cavity.

In some embodiments the concrete reinforcement assembly may have more than the first infill layer and the second infill layer, and may have more than the first hollow metal sleeve and a second hollow metal sleeve. There may be several intermediate infill layers between the first and second infill layers and intermediate hollow metal sleeves between the first and second hollow metal sleeves for added energy absorption.

In some embodiments the first hollow metal sleeve 101, the second hollow metal sleeve 103, and the anchor bar 102 may comprise steel materials including, but not limited to carbon steel, alloy steel, high strength steel, or the like to withstand forces applied to the concrete reinforcement assembly 100. Each hollow metal sleeve and the anchor bar may comprise of different steel materials.

In some embodiments, a longitudinal length of the first hollow metal sleeve 101 and the second hollow metal sleeve 103 is the same as a longitudinal length of the hollow cavity. In some embodiments, a ratio of a longest cross sectional length of the anchor bar 102 to a longitudinal length of the hollow cavity ranges from 1:20-1:50, 1:25-1:45, 1:30-1:40, or 1:35-1:38. In some embodiments, the anchor bar 102 may be longer in length than the hollow cavity by at least 5%-50%, at least 10%-40%, 15%-35%, 20%-30%, or 25%-28%, where 100% is the total length of the anchor bar.

Some embodiments may include the concrete reinforcement assembly 100, in which a cross section of the anchor bar 102 has a shape similar to a cross section 101 of the first hollow metal sleeve 101. A shape may include, but is not limited to an oval, circle, rectangle, hexagon, octagon, or other multi-sided polygon. The second hollow metal sleeve 103 may be a shape similar to the cross sections of the anchor bar and the first hollow metal sleeve 101, but also may be a different shape, such as an oval, circle, rectangle, hexagon, octagon, or other multi-sided polygon. In some embodiments the anchor bar 102, the first hollow metal sleeve 101, and the second hollow metal sleeve 103 are cylindrical.

Some embodiments may include the concrete reinforcement assembly 100 having infill material comprising at least one reinforcing material selected from the group consisting of elastomeric polymer, glass fiber epoxy composite, carbon nanotube epoxy composite, and epoxy. The purpose of the reinforcing material is to introduce stabilizing materials to the infill material to improve the energy absorption properties. Generally, the infill material is considered a nonlinear deformable material thus enabling large distortions to the material, however, including one reinforcing material into the infill material can improve strength, deformability, and/or longevity. Examples of the elastomeric polymer may include, but is not limited to polyisoprene, ethylene propylene rubber, polyacrylic rubber, fluorosilicone rubber, butyl rubber, chloroprene, nitrile rubber, or ethylene-vinyl acetate. The glass fiber epoxy composite may include, but is not limited to microspheres of glass fiber, chopped glass fiber, or woven glass fiber. The carbon nanotube epoxy composite may include, but is not limited to single-wall nanotubes, multi-wall nanotubes, torus nanotubes, or hybridized carbon nanotubes. The epoxy that may be used in the infill material may include bisphenol A epoxy, bisphenol F epoxy, novolac epoxy, aliphatic epoxy or glycidylamine epoxy. Epoxy resins may be reacted with themselves through catalytic homopolymerisation, or with a wide range of co-reactants or curing agents that include polyfunctional amines, acids, and acid anhydrides, phenols, alcohols and thiols. The mass to volume ratio of the reinforcing material to the total volume of the infill material may be approximately 1%-75%, approximately 5%-65%, approximately 10%-50%, approximately 20%-40%, or approximately 30%-35%.

Some embodiments may include the concrete reinforcement assembly 100 having infill material comprising at least one anti-corrosive additive selected from the group consisting of a polythiophene, calcium sulfonate, barium sulfonate, or an amine. The purpose of the anti-corrosive additive is to reduce corrosive effects of water and salt in an environment surrounding the concrete structure.

Some embodiments may include the concrete reinforcement assembly 100 in which an elastic modulus ratio of the anchor 102 bar to the infill material is between 8-25, 10-22, 12-20, or 15-18. The elastic modulus is a number that measures an object or substance's resistance to being deformed elastically (i.e., non-permanently) when a force is applied to it.

In some embodiments, the first infill layer and the second infill layer may be comprised of infill material comprised of different reinforcing material.

In some embodiments, the second hollow metal sleeve 103 may have a plurality of mechanical anchors 107 attached to an outer surface of the second hollow metal sleeve 103. The mechanical anchors 107 are adapted to secure the concrete reinforcement assembly to the hollow cavity in the concrete structure 106 by opening outwardly from the outer surface of the second hollow metal sleeve 103. The mechanical anchors 107 may be attached to the outer surface of the second hollow metal sleeve 103 by a hinge. The hinge enables the mechanical anchors 107 to adopt an open position or closed position. When in the open position the mechanical anchors 107 can extend outwardly into a concrete wall surrounding the hollow cavity in which the assembly 100 may be placed. In some embodiments, the mechanical anchors 107 may be comprised of high strength steel or the like to withstand forces applied to the concrete reinforcement assembly 100. The mechanical anchors 107 may lay flat against the outer surface of the second hollow metal sleeve 103 prior to installation and open upon installation of the anchor bar 102 when the anchor bar 102 engages a trigger button or a mechanical trigger, such as a lever or the like.

In some embodiments, the mechanical anchors 107 may be attached to the outer surface of the second hollow metal sleeve 103 at a variety of horizontally and vertically separated levels. The mechanical anchors 107 may be separated from each other by a distance of 2 cm-50 cm, 5 cm-45 cm, 10 cm-40 cm, 15 cm-35 cm, or 20 cm-30 cm. The mechanical anchors 107 may be distributed randomly or in a regular pattern over the outer surface area of the second hollow metal sleeve 103. The mechanical anchors 107 may cover 1%-80%, 5%-70%, 10%-60%, 15%-50%, or 20%-40% of the outer surface area of the second hollow metal sleeve 103. The mechanical anchors 107 may extend into the hollow cavity by 1 mm-300 mm, 10 mm-280 mm, 25 mm-250 mm, 50 mm-225 mm, 75 mm-200 mm, 100 mm-175 mm, or 125 mm-150 mm.

In some embodiments of the concrete reinforcement assembly, the infill material may separate from the first and second hollow metal sleeves and the anchor bar. For example, the concrete reinforcement assembly may be prepared as the solid pieces of the first and second hollow metal sleeve and the anchor bar with a separate container of the infill material. At installation the infill material may be disposed as described herein in order to form the concrete reinforcement assembly at a construction site where the assembly is required.

The present disclosure is further directed to a method for repairing a damaged concrete anchor. The method includes removing the damaged concrete anchor from a hollow cavity in a concrete structure and inserting the concrete reinforcement assembly 100. The concrete reinforcement assembly 100 may be installed by inserting the second hollow metal sleeve 103 into the hollow cavity, the first hollow metal sleeve 101 is installed by nesting the first hollow metal sleeve 101 concentrically within the second hollow metal sleeve 103, then disposing an infill material in between the first hollow metal sleeve 101 and the second hollow metal sleeve 103. The infill material is as described previously herein. The second hollow metal sleeve 103 may have an outer surface attached to a plurality of mechanical anchors 107 by a plurality of hinges, as described herein. The anchor bar 102 is installed concentrically within the first hollow metal sleeve 101 such that the anchor bar 102 is moveable along a longitudinal axis of the first hollow metal sleeve 101, and disposing an infill material in between the first hollow metal sleeve 101 and the anchor bar 102.

The disposing may be accomplished by pouring from a vessel containing the infill material, extruding from a tube containing the infill material manually or from a pressure applied by a piston, as in a dispensing gun or caulking gun.

In some implementations, the method may further include resurfacing the hollow cavity in the concrete structure after removing the damaged concrete anchor. The resurfacing may be accomplished by a drill, abrasive grinding tool, or sanding and then followed by flushing with forced air at a pressure sufficient to remove particles remaining in the hollow cavity.

In some implementations of the method, the insertion of the anchor bar 102 triggers a plurality of mechanical anchors 107 to open. The plurality of mechanical anchors 107 may be connected by a lever mechanism enabling the mechanical anchors 107 to open on the outer surface of the second hollow metal sleeve 103 upon the insertion of the anchor bar 102 and triggering of the lever mechanism by a switch. The lever mechanism may be described as a mechanical linkage in which one or more connected levers' motion creates movement of an object. The switch may be configured to operate by a button or a toggle to operate the lever mechanism. The lever mechanism may include, but is not limited to pistons, pulleys, chains, or connecting rods.

An aspect of the present disclosure is directed to a non-transitory computer readable medium having stored thereon a program that, when executed by a computer, causes the computer to carry out a method of determining a cyclic response factor of a concrete reinforcement assembly in a concrete structure.

Figure 3:
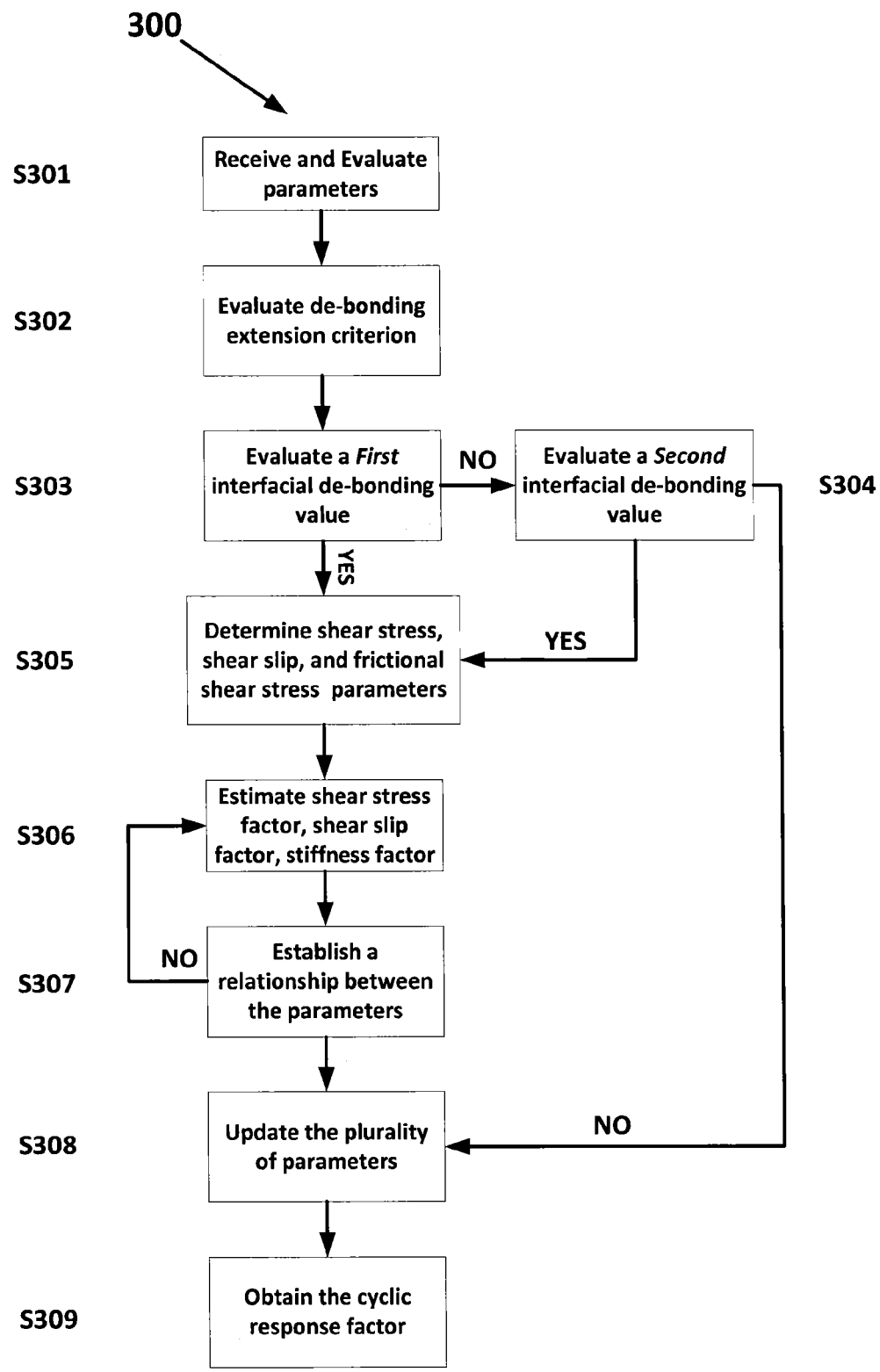
FIG. 3 is a flowchart of a method to determine the cyclic response factor of the concrete reinforcement assembly.

Referring now to FIG. 3, which depicts the method 300 of determining the cyclic response factor of the concrete reinforcement assembly 100 in the concrete structure; at S301 the method receives a plurality of parameters of the concrete reinforcement assembly and evaluates the plurality of parameters of the concrete reinforcement assembly. The plurality of parameters may be inputted directly, retrieved from a database of stored values, or received by sensors that are actively transmitting the information to a device that translates the information into readable values and displayed on a display, a mobile device, or a computer screen.

In some implementations, the plurality of parameters of the concrete reinforcement assembly includes at least one of a geometrical parameter of the concrete reinforcement assembly, an elastic modulus ratio of the concrete reinforcement assembly 100, and a loading history of the concrete structure. The geometrical parameter of the concrete reinforcement assembly may include, but is not limited to the ratio of the longest cross sectional length of the anchor bar 102 to the longitudinal length of the hollow cavity, a perimeter of the cross section of the anchor bar 102, the perimeter of the cross section of the first hollow metal sleeve 101, or the perimeter of the cross section of the second hollow metal sleeve 103, a thickness of the first infill layer 104 or the second infill layer 105, thickness of a wall of the first hollow metal sleeve 101 or the second hollow metal sleeve 103. The elastic modulus ratio may include, but is not limited to the quotient of the elastic modulus of the anchor bar 102 and the infill material or the quotient of the elastic modulus of the infill material and a yield strength of the infill material, and the quotient of the yield strength of the first infill layer 104 to the yield strength of the second infill layer 105. The loading history of the concrete structure is a plurality of measurements of displacements that have occurred to the structure that may affect a future performance of the concrete reinforcement assembly.

In step S302 evaluation of a de-bonding extension criterion is carried out by assessing equations 201, 202, and 203 in FIG. 2. The de-bonding extension criterion is an evaluation of whether a force applied to the concrete reinforcement assembly by an applied stress ($q_{r1}$, $q_{r2}$) will overcome the material properties, such as the yield strength ($q_{y1}$, $q_{y2}$), of the infill material in the concrete reinforcement assembly 100, resulting in damage of the concrete reinforcement assembly 100.

In step S303 the first interfacial de-bonding value is evaluated in terms of the de-bonding extension criterion and the infill material yield strength. The first interfacial de-bonding value is a quantitative measurement to determine crack formation in the first infill layer. If the first interfacial de-bonding value indicates that the force applied will induce de-bonding in the first infill layer 104 after application of force ("NO" at step S303), then the next step S304 is to evaluate the second interfacial de-bonding value in terms of the de-bonding extension criterion. The second interfacial de-bonding value is a quantitative measurement to determine crack formation in the second infill layer. If the second interfacial de-bonding value indicates that the force applied will induce de-bonding in the second infill layer 105 ("NO" at step S303), then the step S308 is carried out to update the parameters based on the first and second interfacial de-bonding values and in step S309 obtain the cyclic response factor.

Referring again to step S304, if the second interfacial de-bonding value indicates that the force applied will not induce de-bonding in the second infill layer 105 ("YES" at step S304), then the method 300 may proceed to step S305. Similarly, referring again to step S303, if the first interfacial de-bonding value indicates that the force applied will not induce de-bonding in the first infill layer 104 after application of force ("YES" at step S303), then the next step S305 is to determine shear stress, shear slip, and frictional shear stress parameters. The shear stress, shear slip and frictional shear stress parameters may be determined with equation 401 listed in FIG. 4. The equation listed in 401 may be employed with the material properties of the infill materials such as an elastic stiffness ($k_e$) and the yield strength ($q_{yi}$). Upon determining the shear stress, shear slip, and frictional shear stress parameters the method 300 proceeds to S306 to estimate a shear stress factor, shear slip factor, and a stiffness factor.

Figure 5:
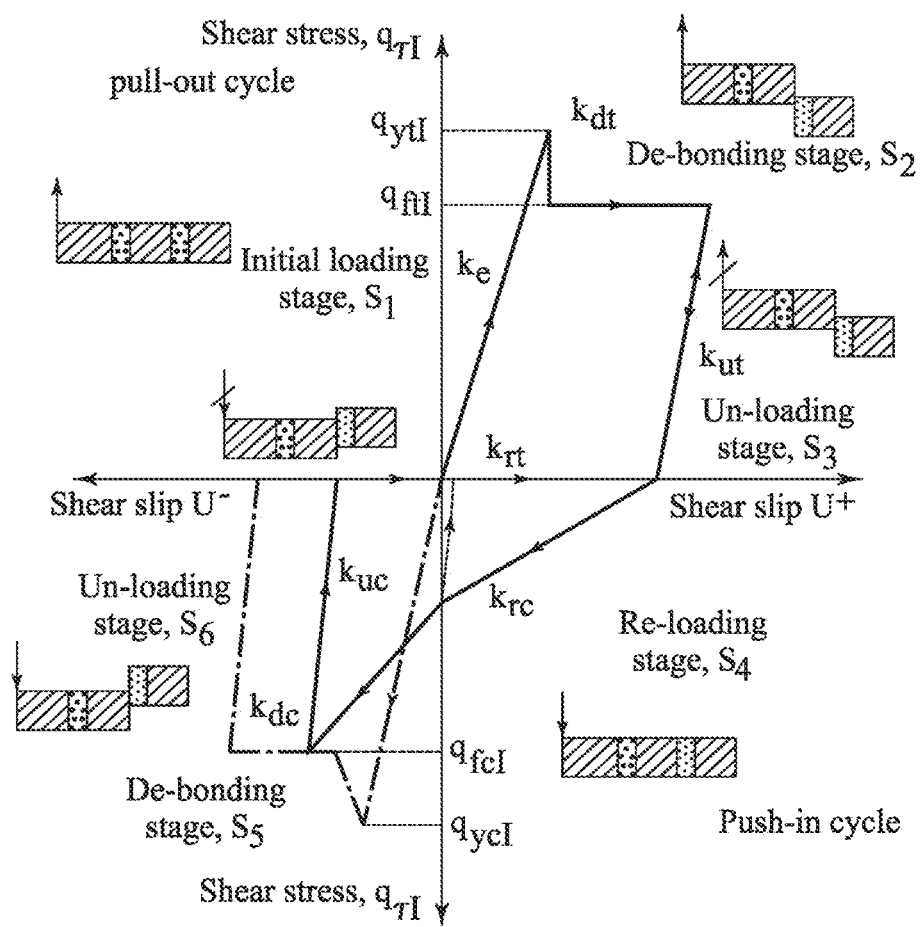
FIG. 5 is an exemplary diagram of a shear stress forces versus shear slip forces in a cyclic response of the concrete reinforcement assembly.

In S306, FIG. 4 equations 402, 403, 404, 405, and 406 may be employed to estimate the shear stress factor (P*), shear slip factor (U*), and the stiffness factor (k). The equations 402, 403, 404, 405, and 406 may be employed sequentially or individually to provide an estimate of the shear stress factor (P*), shear slip factor (U*), and the stiffness factor (k) for the loading history. The stiffness factor may take many forms including, but is not limited to an elastic stiffness factor ($k_e$), a deterioration stiffness factor ($k_{dt}$), a recovery stiffness factor ($k_{rec}$), and a de-bonding compressive stress stiffness factor ($k_{dc}$). FIG. 5 depicts an exemplary diagram of shear stress versus shear slip and stiffness factors that are in effect in various parts of the diagram. FIG. 6 depicts alternate equations that may be employed to estimate the shear stress factor, shear slip factor, and the stiffness factor. The equations of FIG. 4 and FIG. 6 may be repeated by a trial and error process to achieve estimates of the shear stress factor (P*), shear slip factor (U*), and the stiffness factor (k) that fulfill a coefficient of determination (i.e. $R^2$) or a regression analysis that may occur simultaneously with the estimation. Once the shear stress factor, shear slip factor and the stiffness factor are estimated the next step S307 can proceed.

In step S307 a relationship may be established between the results of the equations in step S306 and the plurality of parameters of the concrete reinforcement assembly 100, the de-bonding extension criterion, the shear stress parameter, shear slip parameter, and the plurality of frictional shear stress parameters. The relationship may be established by graphically plotting the results of the equations in step S306 with the plurality of parameters of the concrete reinforcement assembly, the de-bonding extension criterion, the shear stress parameter, shear slip parameter, the plurality of frictional shear stress parameters, and cross-referencing the loading history of the concrete reinforcement assembly. If a relationship is not established the method returns to step S306 to estimate the shear stress factor, shear slip factor, and the stiffness factor. Once the relationship is established then the method may proceed to step S308 in which the plurality of parameters are updated with the estimates and proceeds to the last step S309 to obtain a cyclic response factor from the estimates and the plurality of parameters. The cyclic response factor is a value that measures the ability of the concrete reinforcement assembly to resist fatigue under a given force applied. The cyclic response factor may change depending on the plurality of parameters, applied force, loading history, and material properties.

Figure 7:
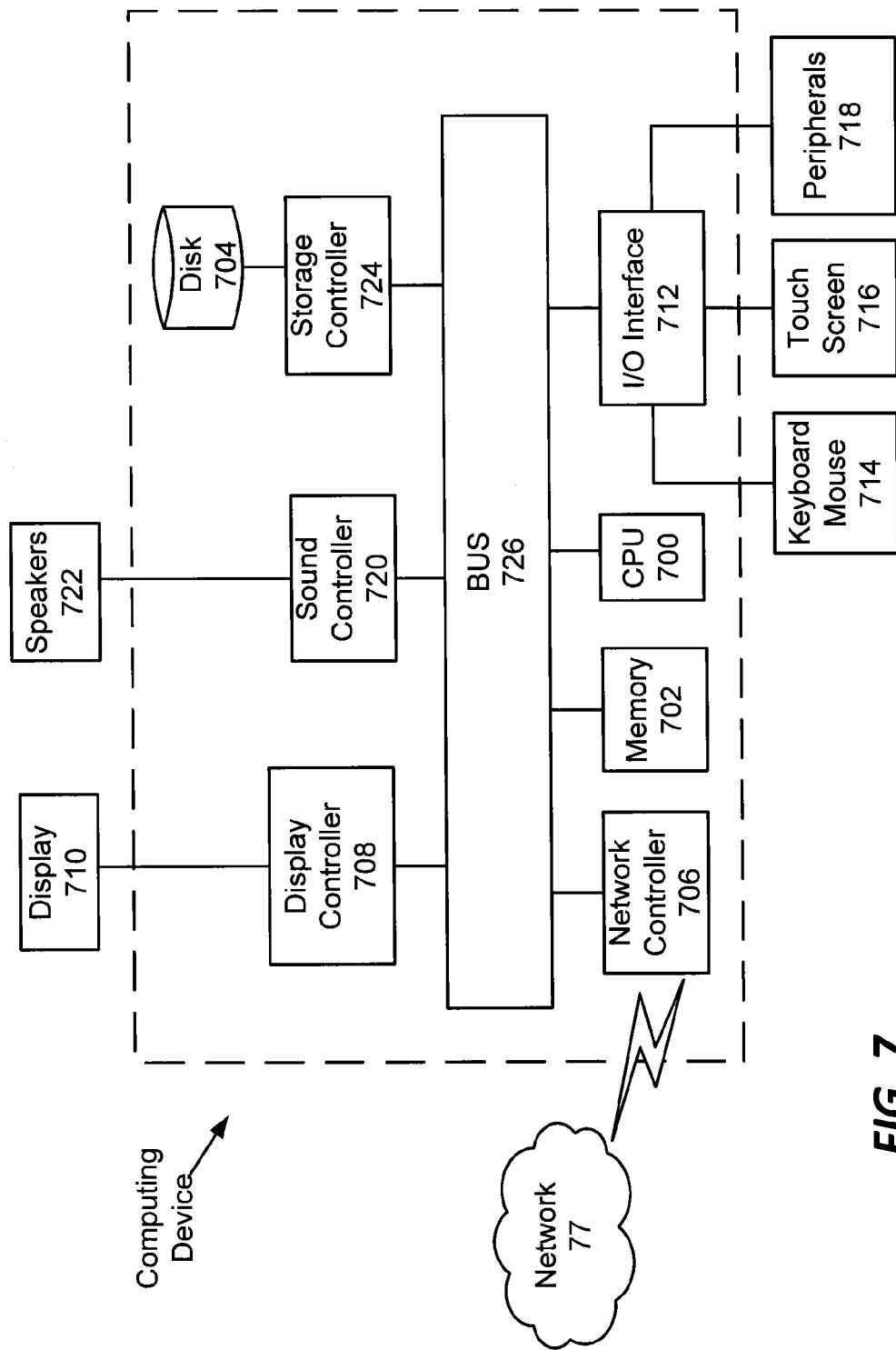
FIG. 7 is an exemplary schematic diagram of a computing device, according to certain embodiments, that can execute the instructions of a non-transitory computer readable media to carry out a method of determining a cyclic response factor.

In FIG. 7, the computing device includes a CPU 700 which performs the steps described above. Processes and instructions to carry out the method may be stored in memory 702. These processes and instructions may also be stored on a storage medium disk 704 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claimed advancements may be provided as a utility application, background daemon, or component of an operating system, or combination thereof, executing in conjunction with CPU 700 and an operating system such as Microsoft Windows 7, UNIX, Solaris, LINUX, Apple MAC-OS and other systems known to those skilled in the art.

The hardware elements in order to achieve the computing device may be realized by various circuitry elements, known to those skilled in the art. For example, CPU 700 may be a Xenon or Core processor from Intel of America or an Opteron processor from AMD of America, or may be other processor types that would be recognized by one of ordinary skill in the art. Alternatively, the CPU 700 may be implemented on an FPGA, ASIC, PLD or using discrete logic circuits, as one of ordinary skill in the art would recognize. Further, CPU 700 may be implemented as multiple processors cooperatively working in parallel to perform the instructions of the method described above.

The computing device in FIG. 7 also includes a network controller 706, such as an Intel Ethernet PRO network interface card from Intel Corporation of America, for interfacing with network 77. As can be appreciated, the network 77 can be a public network, such as the Internet, or a private network such as an LAN or WAN network, or any combination thereof and can also include PSTN or ISDN subnetworks. The network 77 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing device further includes a display controller 708, such as a NVIDIA GeForce GTX or Quadro graphics adaptor from NVIDIA Corporation of America for interfacing with display 710, such as a Hewlett Packard HPL2445w LCD monitor. A general purpose I/O interface 712 interfaces with a keyboard and/or mouse 714 as well as a touch screen panel 716 on or separate from display 710. General purpose I/O interface also connects to a variety of peripherals 718 including printers and scanners, such as an OfficeJet or DeskJet from Hewlett Packard.

A sound controller 720 is also provided in the computing device, such as Sound Blaster X-Fi Titanium from Creative, to interface with speakers/microphone 722 thereby providing sounds and/or music.

The general purpose storage controller 724 connects the storage medium disk 704 with communication bus 726, which may be an ISA, EISA, VESA, PCI, or similar, for interconnecting all of the components of the computing device. A description of the general features and functionality of the display 710, keyboard and/or mouse 714, as well as the display controller 708, storage controller 724, network controller 706, sound controller 720, and general purpose I/O interface 712 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 8.

Figure 8:
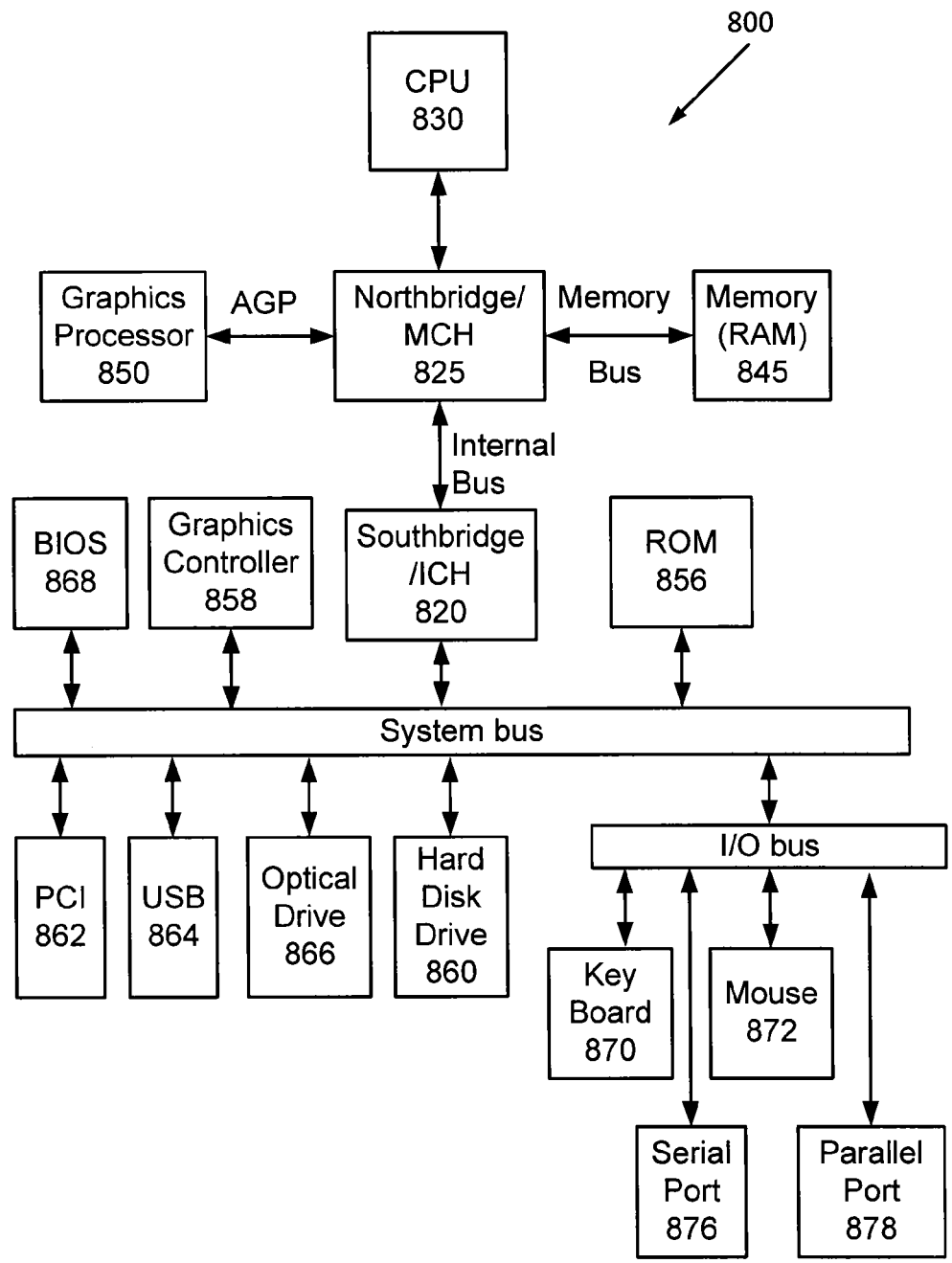
FIG. 8 is an exemplary schematic diagram of a data processing system, according to certain embodiments, for determining the cyclic response factor.

FIG. 8 shows a schematic diagram of a data processing system, according to certain embodiments, for determining the cyclic response factor. The data processing system is an example of a computer in which code or instructions implementing the processes of the illustrative embodiments may be located.

In FIG. 8, data processing system 800 employs a hub architecture including a north bridge and memory controller hub (NB/MCH) 825 and a south bridge and input/output (I/O) controller hub (SB/ICH) 820. The central processing unit (CPU) 830 is connected to NB/MCH 825. The NB/MCH 825 also connects to the memory 845 via a memory bus, and connects to the graphics processor 850 via an accelerated graphics port (AGP). The NB/MCH 825 also connects to the SB/ICH 820 via an internal bus (e.g., a unified media interface or a direct media interface). The CPU Processing unit 830 may contain one or more processors and even may be implemented using one or more heterogeneous processor systems.

Figure 9:
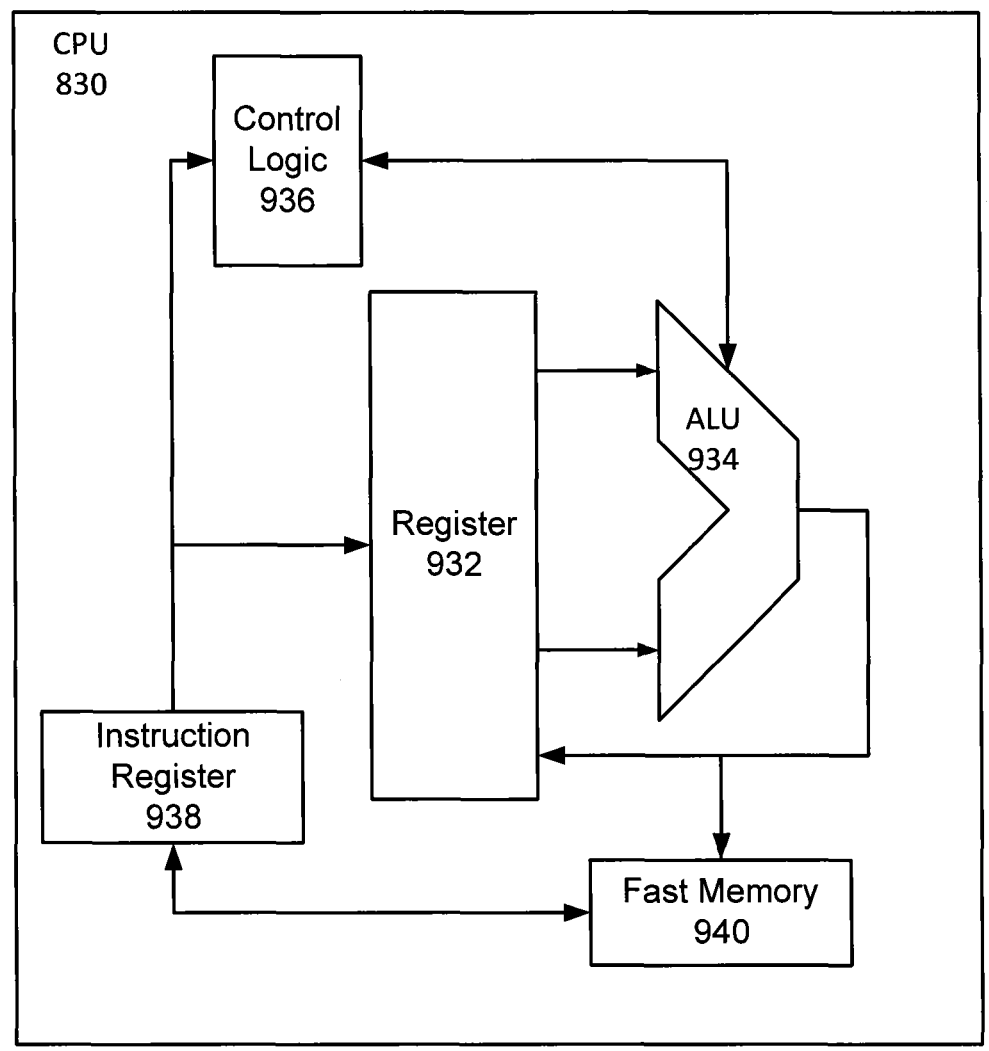
FIG. 9 is an exemplary schematic diagram of an implementation of CPU 830.

For example, FIG. 9 shows one implementation of CPU 830. In one implementation, the instruction register 938 retrieves instructions from the fast memory 940. At least part of these instructions are fetched from the instruction register 938 by the control logic 936 and interpreted according to the instruction set architecture of the CPU 830. Part of the instructions can also be directed to the register 932. In one implementation the instructions are decoded according to a hardwired method, and in another implementation the instructions are decoded according a microprogram that translates instructions into sets of CPU configuration signals that are applied sequentially over multiple clock pulses. After fetching and decoding the instructions, the instructions are executed using the arithmetic logic unit (ALU) 934 that loads values from the register 932 and performs logical and mathematical operations on the loaded values according to the instructions. The results from these operations can be feedback into the register and/or stored in the fast memory 940. According to certain implementations, the instruction set architecture of the CPU 830 can use a reduced instruction set architecture, a complex instruction set architecture, a vector processor architecture, a very large instruction word architecture. Furthermore, the CPU 830 can be based on the Von Neuman model or the Harvard model. The CPU 830 can be a digital signal processor, an FPGA, an ASIC, a PLA, a PLD, or a CPLD. Further, the CPU 830 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 8, the data processing system 800 can include that the SB/ICH 820 is coupled through a system bus to an I/O Bus, a read only memory (ROM) 856, universal serial bus (USB) port 864, a flash binary input/ output system (BIOS) 868, and a graphics controller 858. PCI/PCIe devices can also be coupled to SB/ICH 888 through a PCI bus 862.

The PCI devices may include, for example, Ethernet adapters, add-in cards, and PC cards for notebook computers. The Hard disk drive 860 and CD-ROM 866 can use, for example, an integrated drive electronics (IDE) or serial advanced technology attachment (SATA) interface. In one implementation the I/O bus can include a super I/O (SIO) device.

Further, the hard disk drive (HDD) 860 and optical drive 866 can also be coupled to the SB/ICH 820 through a system bus. In one implementation, a keyboard 870, a mouse 872, a parallel port 878, and a serial port 876 can be connected to the system bust through the I/O bus. Other peripherals and devices that can be connected to the SB/ICH 820 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

The functions and features described herein may also be executed by various distributed components of a system. For example, one or more processors may execute these system functions, wherein the processors are distributed across multiple components communicating in a network. The distributed components may include one or more client and server machines, which may share processing, as shown on FIG. 10, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

Figure 10:
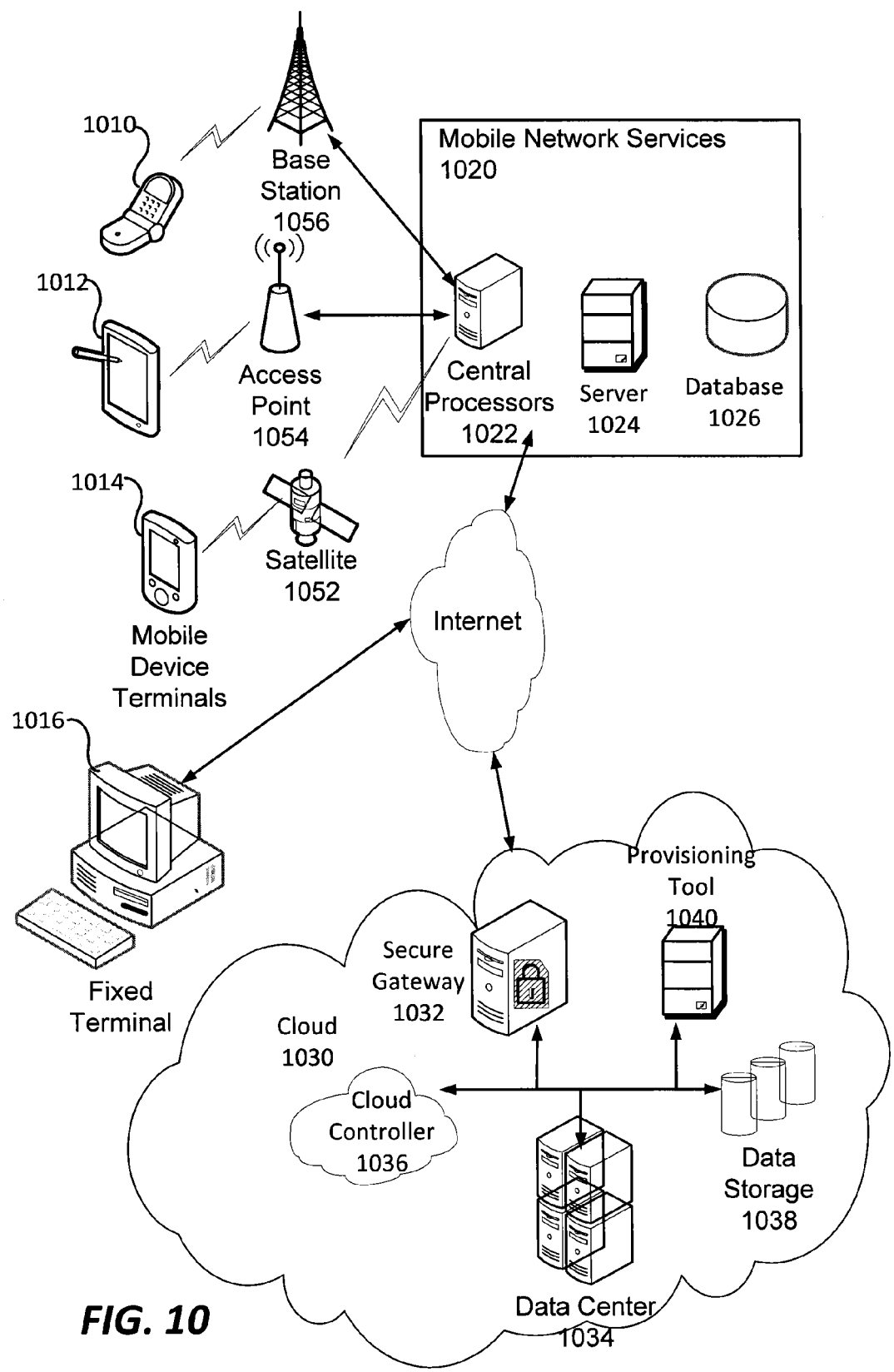
FIG. 10 is an exemplary schematic diagram of distributed components of a system employed for determining the cyclic response factor.

The method described in FIG. 3 may be completely performed by the circuitry included in the single computing device shown in FIG. 7 or the chipset as shown in FIG. 8, or the method may be completely performed in a shared manner distributed over the circuitry of any plurality of the devices shown in FIG. 10.

The above-described hardware description is a non-limiting example of corresponding structure for determining the cyclic response factor described herein.

The examples below are intended to further illustrate protocols for determining a cyclic response factor for a concrete reinforcement assembly and are not intended to limit the scope of the claims.

EXAMPLE 1

Loading History

Figure 11:
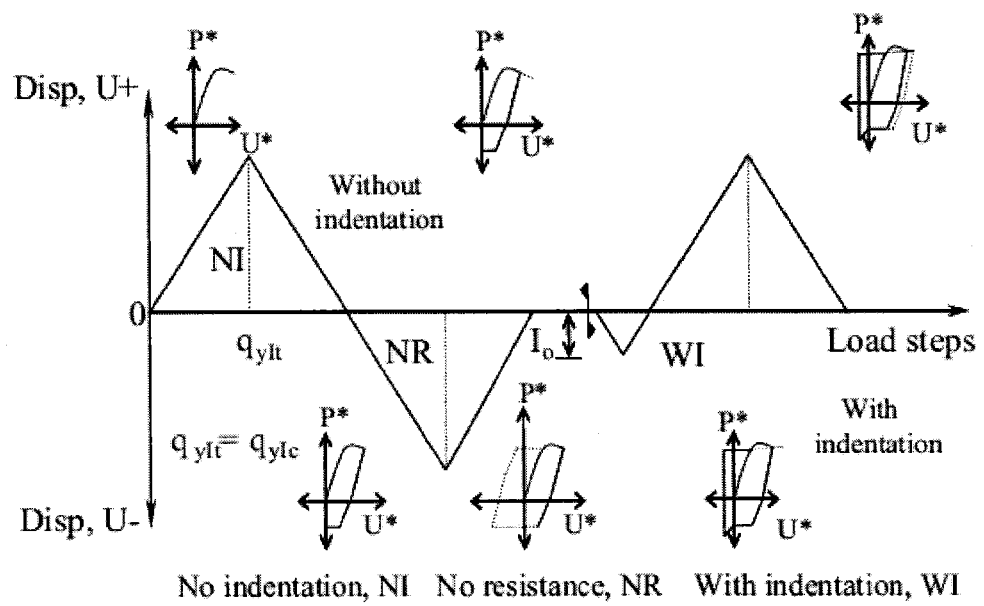
FIG. 11 is an exemplary diagram of a loading history.

FIG. 11 shows an exemplary loading history employed for plotting the cyclic response of a concrete reinforcement assembly along with a snapshot of a load-displacement response. The loading history has been divided in three parts. The first part represents a condition without indentation (NI) where the concrete at a bottom of the hollow cavity is strong enough that it does not become crushed under an applied load, hence resulting in no negative displacement as seen on FIG. 11. The second part is the one with no resistance (NR) where the anchor bar never comes in contact with the bottom of the hollow cavity, and hence, no resistance is offered against negative displacements. The third part is with indentation (WI) where the bottom of the hollow cavity crushes slightly to allow for negative displacements.

Figure 12B:
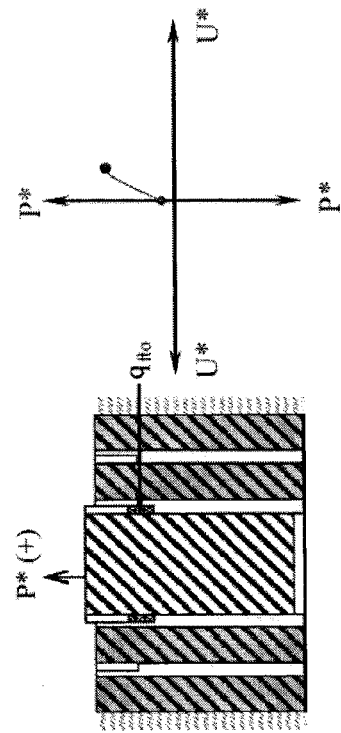
FIG. 12B is an exemplary schematic diagram of a step in the loading history, which depicts interfacial de-bonding.
Figure 12D:
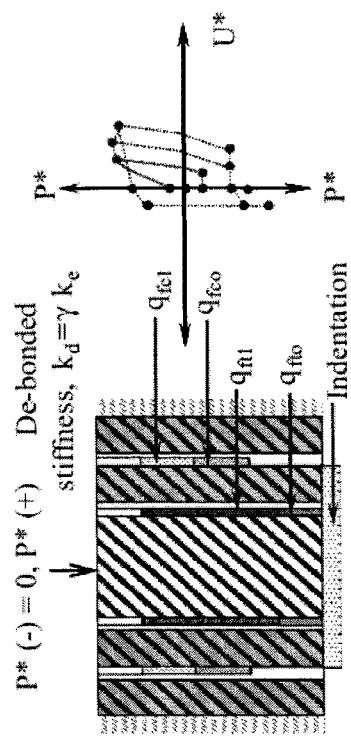
FIG. 12D is an exemplary schematic diagram of a step in the loading history resulting in the concrete reinforcement assembly failure.
Figure 12A:
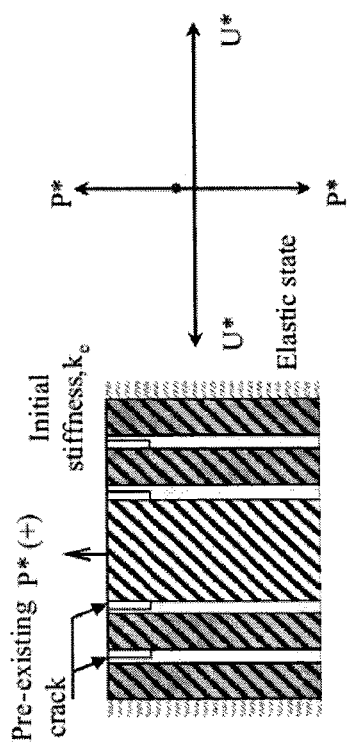
FIG. 12A is an exemplary schematic diagram of a pull-out step in the loading history.

FIG. 12A, FIG. 12B, FIG. 12C, and FIG. 12D shows a diagram of cyclic response of the concrete reinforcement assembly described herein along with the step-by-step development of the load-displacement response. The cyclic response starts with the pull-out load application; initially, the load is within the elastic limit of the infill material, so there is no de-bonding at the interface as shown in FIG. 12A. Preexisting cracks representing artificial notches are assumed at the top of infill layers to identify crack location and stabilize crack propagation. Then, after reaching the yield strength of infill material, interfacial de-bonding occurs as shown in FIG. 3b over the length $\Delta a$ and the new position of the de-bonded interface shifts by $a_N = a_P + \Delta a$ where the subscript N refers to the new position and the subscript P refers to the previous location of the de-bonded infill interface. The bond strength reduces to a reduced value of bond stress depicting the de-bonding in terms of reduction in bond condition at the interface, $q_f$ to. Where $q_{fto}$ is frictional shear stress acting at the interface after de-bonding, the subscript t indicates that the de-bonding in tension has taken place while the subscript o represents the first time de-bonding of the interface.

Figure 12C:
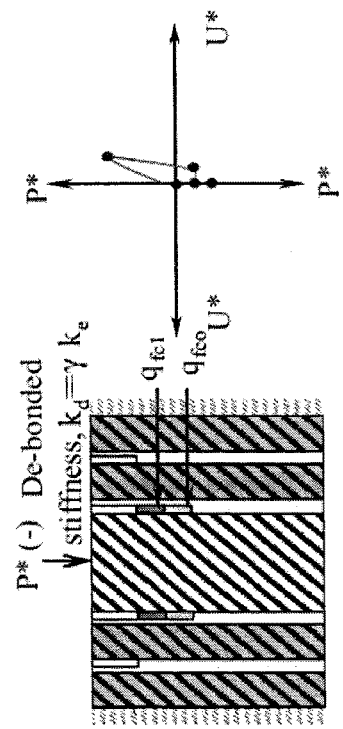
FIG. 12C is an exemplary schematic diagram of a step in the loading history, which depicts a shear force after interfacial de-bonding.

After the pull-out load reverses, the push-in loading starts and stiffness recovery ($k_{rec}$) takes place due to the crack closure owing to the lateral pressure effect included in the form of increase in stiffness and increased constant shear stress at the interface, $q_{fc1}$, where $q_{fc1}$ is the increased constant frictional shear stress acting at the previously de-bonded interface during the push-in loading. The subscript c represents that the push-in cycle is in progress while the subscript 1 indicates that this part of infill interface has already de-bonded previously as shown in FIG. 12C. During the push-in cycle, the previously de-bonded interface closes partially, resulting in partial recovery in stiffness due to the lateral pressure and Poisson's effect. However, upon further increase in the push-in load, the yield strength of the infill material in the reverse direction is achieved; thus, resulting in de-bonding during the push-in cycle over the length $\Delta a$ and the de-bonded interface further shifts by $a_N = a_P + \Delta a$. This is followed by the reversal of applied loading direction, upon which the stiffness is revised again to represent the de-bonding deterioration of the infill. Similar process is repeated up to the point of $U_{peak}$, after which indentation representing the concrete crushing at the bottom of the drilled hole and the slight buckling of the steel bar at the top of the drilled hole is assumed to have occurred. Indentation results in the negative displacements. After the anchor bar touches the bottom of the concrete hole, two possibilities can be encountered: one that the load further increases in which the load increases resulting in de-bonding in the reverse direction but the negative displacements are restricted; the second option is that the loading changes direction at that instance, which will result in a similar repetition of cycle as mentioned before.

The aforementioned process continues till the complete de-bonding of the single interface takes place. After which during the pull-out, the only resistance offered by the anchor infill assembly is the frictional shear force. However, during the push-in loading cycle, partial recovery of stiffness takes place due to partial crack closure owing to the lateral pressure effect. Simultaneously, during the push-in cycle, the second infill interface that was inactive till this point becomes active and starts resisting the applied push-in load resulting in de-bonding in the reverse direction accompanied with absorption of extra energy and providing a larger failure during the push-in cycle as shown in FIG. 12D. Hence, the presence of second infill interface becomes justified during this phase of the cyclic pull-out push-in response during which both the infill interfaces help in energy absorption.

EXAMPLE 2

Cyclic Shear-Lag Material Model

FIG. 5 represents a piecewise linear cyclic pull-out push-in shear-lag material model representing the local bond behavior of the post-installed anchor bar along with the step-by-step conceptual local response of the anchor-infill assembly presented at each stage. The vertical axis represents the shear stress, $q_r$, and the horizontal axis represents the shear slip, U. The positive part of the cycle represents pull-out while the negative part represents push-in. The material model is divided into two categories, namely with indentation and without indentation. The cyclic response of each category is further broken into six paths starting with S1, the elastic loading cyclic, during which the stiffness is taken as $k_e$ representing the initial elastic stiffness of the interface before any de-bonding. After reaching the tensile yield strength, $g_{yrt}$, there is a sudden drop in the force accompanied with the de-bonding at the interface (S2) and reduction in stiffness to $k_{dt}$. S3 represents the unloading stage referring to the stage when the pull-out load is removed and push-in loading starts. S4 represents the reloading stage under push-in loading, and stiffness is partially recovered during this stage due the lateral pressure acting on the infill material, which results in the closing of previously de-bonded infill interface, resulting in a temporary rise in the stiffness of the infill material. This is depicted by the difference in slope of the line during push-in cycle. At this stage, there are two possibilities for the push-in loading path. One, if the condition of indentation is satisfied, i.e., $U=U_{peak}$, it will move into the negative slip direction and the only resistance offered during the push-in loading will be the frictional shear resistance. The second, if the condition of indentation is not satisfied, then the loading can either increase till it reaches the yield strength in the reverse direction resulting in further propagation of de-bonded length (S5) of the adjacent infill interface or the loading reverses direction and pull-out loading cycle begins again shown by unloading cycle (S6). After reaching the stage 5, the push-in loading reverses and the pull-out begins as given by stage 6.

Figure 13A:
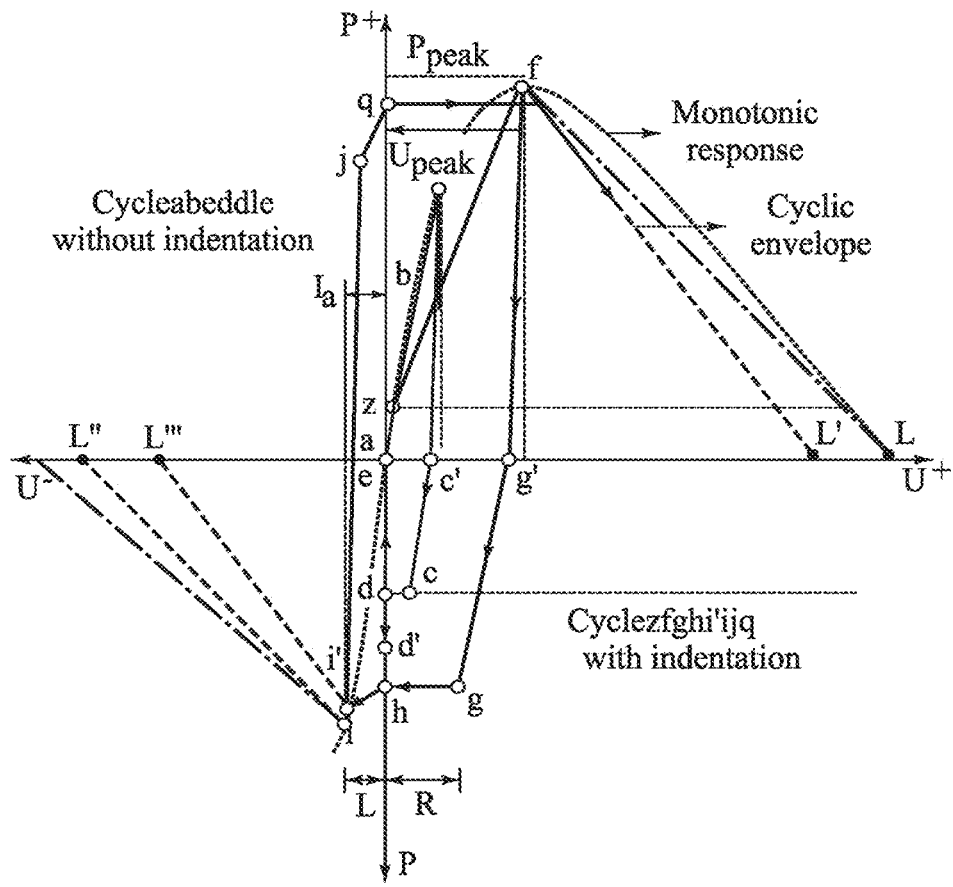
FIG. 13A is exemplary schematic diagram of the pull-out push-in response curve.
Figure 13B:
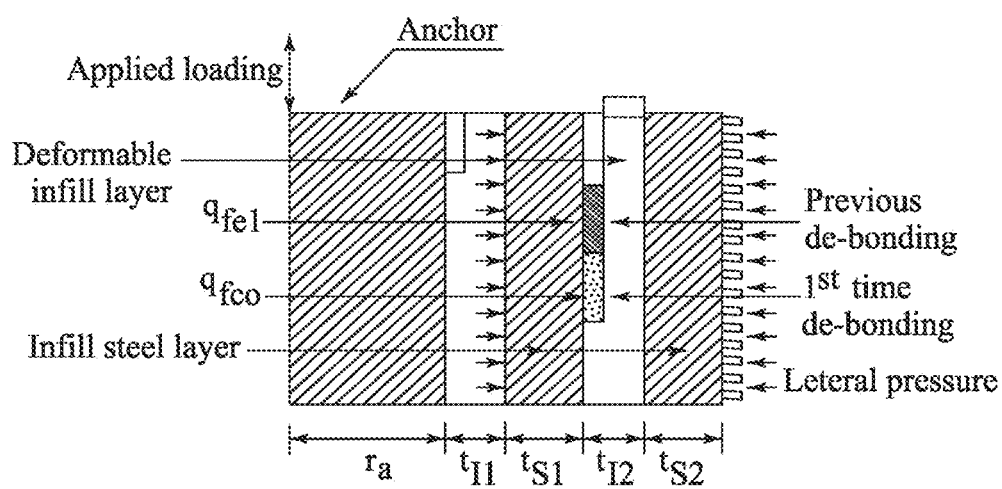
FIG. 13B is an exemplary schematic of Poisson's effect in the concrete reinforcement assembly.

The aforementioned piecewise linear cyclic pull-out push-in shear-lag material model is used to plot the cyclic response of the post-installed anchor bar. Once complete de-bonding of a single interface takes place, the adjacent second interface becomes active during the push-in loading cycle. However, during the pullout loading cycle, the only resistance offered by the infill interface is the frictional shear resistance. FIG. 13A represents the cyclic pull-out push-in load-displacement response of the anchor-infill assembly subjected to cyclic loading. The cyclic response has been divided into two classes (i.e. cycle with indentation represented by abc'cdd'e in FIG. 13A and cycle without indentation represented by zfg'ghii'jq in FIG. 13A). The cycle without indentation is divided into six paths while cycle with indentation is divided into nine paths where the stiffness is updated at the beginning of each path to represent the deterioration or recovery of stiffness of the infill interface. The effect of degradation due to loading is incorporated in the form of stiffness reduction upon de-bonding and the effect of lateral pressure is accounted in the form of stiffness recovery and increased constant shear strength of the interface. The cycle without indentation is divided into six paths while cycle with indentation is divided into nine paths where the stiffness is updated at the beginning of each path to represent the deterioration or recovery of stiffness of the infill interface. The effect of degradation due to loading is incorporated in the form of stiffness reduction upon de-bonding and the effect of lateral pressure is accounted in the form of stiffness recovery and increased constant shear strength of the interface. The de-bonding stiffness is assumed to be one-third of the elastic stiffness, i.e., $k_d=\gamma k_e$. The constant frictional shear force is divided into four parts $q_{fto}$, $q_{fco}$, $q_{ft1}$ and $q_{fc1}$·$q_{fto}$ and $q_{fco}$ represent the constant frictional shear force, which is assumed to act at the first time of interface de-bonding, while $q_{ft1}$ and $q_{fc1}$ represent the constant frictional shear force acting on the previously de-bonded interface due to stiffness recovery upon crack closure caused by the lateral pressure as shown in FIG. 13B. Hence, based on the above discussion, the following relationship between $q_{fto}$, $q_{fco}$, $q_{ft1}$ and $q_{fc1}$ is assumed $q_{fco}>q_{fc1}$ and $q_{fto}>q_{ft1}$ where the subscript t represents the pull-out cycle and the subscript c represents the push-in cycle. The rules for plotting each path are formulated using the trial and error approach and are presented in preceding section. FIG. 13B depicts the cross section of the two-layer anchor-infill assembly where $t_{f1}$ and $t_{f2}$ are the thickness of the first and second nonlinear deformable infill layers and tS1 and tS2 are the thicknesses of the first and second steel hollow cylinders surrounding the nonlinear infill layers, respectively. During the push-in loading cycle, the previously de-bonded infill interface closes owing to Poisson's and lateral pressure effect, and this is included into the analytical model in a form of increased constant shear force $q_{fc1}$ acting at previously de-bonded interface. Further increase in the push-in loading results in achieving the yield strength of the infill interfaces, and since the de-bonded length increases, a different constant frictional shear force $q_{fco}$ is assumed to act at the new de-bonded infill interface. Stiffness is revised during plotting of the cyclic response. Stiffness evaluation is undertaken at load reversal points, and stiffness value is updated in order to incorporate the effect of infill interface de-bonding representing infill material deterioration.

EXAMPLE 3

Cyclic Rules Applied

Rules for getting the pull-out push-in cyclic load-displacement response for with- and without-indentation cycles have been formulated based on the piecewise linear cyclic shear-lag material model shown in FIG. 13A. The experimental investigation about the local bond behavior of the deformed steel bar under cyclic loading was the guideline during the formation of the following rules. The cycle without indentation cycle is divided into six paths while the cycle with indentation is divided into nine paths, with stiffness revisal incorporated at each stage in order to represent the stiffness degradation due to de-bonding and stiffness recovery due to lateral pressure effect. First, considering the cyclic pull-out push-in load-displacement response without the indentation which is represented by the loading cycle abc'cdd'e in FIG. 13A, six points recognized for getting this loading cycle are $(P_a,U_a)$, $(P_b,U_b)$, $(P_{c'},U_{c'})$, $(P_c,U_c)$, $(P_d,U_d)$ and $(P_{d'},U_{d'})$. Rules for getting each of these points were developed by trial and error approach and are presented as presented in Table 1.

The aforementioned rules are followed to get the cyclic response of the post-installed anchor bar preindentation. $\alpha$ and $\beta$ are the stability coefficients obtained from the statistical analysis of experimental data and taken equal to 0.2 and 0.02, respectively. For calculation purposes, values are kept the same in the present model as well. Also $\gamma$, $\lambda$, $\zeta$, $\kappa$, $\xi$ and $\iota$ are control coefficients coefficients obtained by trial and error taken equal to $\frac{1}{3}$, 2, 4, 0.5, 0.05 and 0.1, respectively. Using the aforementioned methodology, the cyclic pull-out push-in rules for the with indentation part of the cyclic response are also formulated as shown below. This cycle is represented by the loading cycle zfg'ghi'ijq as shown in FIG. 13A and has been further subdivided into nine paths with stiffness update at each stage to accurately represent the deterioration and recovery of stiffness of the infill material. These points are recognized as $(P_z,U_z)$, $(P_f,U_f)$, $(P_{g'},U_{g'})$, $(P_g,U_g)$, $(P_h,U_h)$, $(P_{i'},U_{i'})$, $(P_i,U_i)$, $(P_j,U_j)$ and $(P_q,U_{q'})$. The rules for the points listed above are presented in Table 1.

TABLE 1

(1) $\quad P_a = k_{ini}U_a$, $U_a = \dfrac{q_{yi}}{k_{ini}}$, $a = 0$, $q_f = 0$, $k_{ini} = k_e$ (2) $\quad P_b = U_b k_{dt}(1 - \lambda\alpha)$, $U_b =$ given, $a > 0$, $k_{dt} = \gamma k_{ini}$ (3) $\quad P_{c'} = 0$, $U_{c'} = U_b - (1 + \alpha)\left(\dfrac{P_b}{\beta}\right)k_{rec}$, $k_{rec} = k_e - k_{dt}$ (4) $\quad P_c = -(1 + \lambda\alpha)P_c$, $U_c = U_{c'} - (1 + \alpha)\left(\dfrac{P_b}{\varsigma\beta k_{rec}}\right)$ (5) $\quad P_d = P_c$, $U_d = 0$
(6) $\quad P_{d'} = -\alpha k_{dc}U_c$, $U_{d'} = 0$, $k_{dc} = k_{dt}$
(7) $\quad P_z = \beta P_{peak}$, $U_z = \beta U_{peak}$
(8) $\quad P_f = (1 - \lambda\alpha)k_{dt}U_f$, $U_f =$ given, $k_{dt} = \gamma k_{ini}$ (9) $\quad P_{g'} = 0$, $U_{g'} = U_f - (1 + \alpha)\left(\dfrac{P_f}{\beta k_{rec}}\right)$, $k_{rec} = k_e - k_{dt}$

(10) $\quad P_g = -(1 + \alpha)P_f$, $U_g = U_{g'} - (1 + \alpha)\left(\dfrac{P_b}{\kappa\beta k_{rec}}\right)$

(11) $\quad P_h = P_{g'}$, $U_h = 0$
(12) $\quad P_{i'} = -(\alpha - \xi)k_{dc}U_f$, $U_{i'} = -\alpha U_f$
(13) $\quad P^* = (1 + \alpha)P'$, $U^* = -(\alpha + \iota)U_f$

Figure 14A:
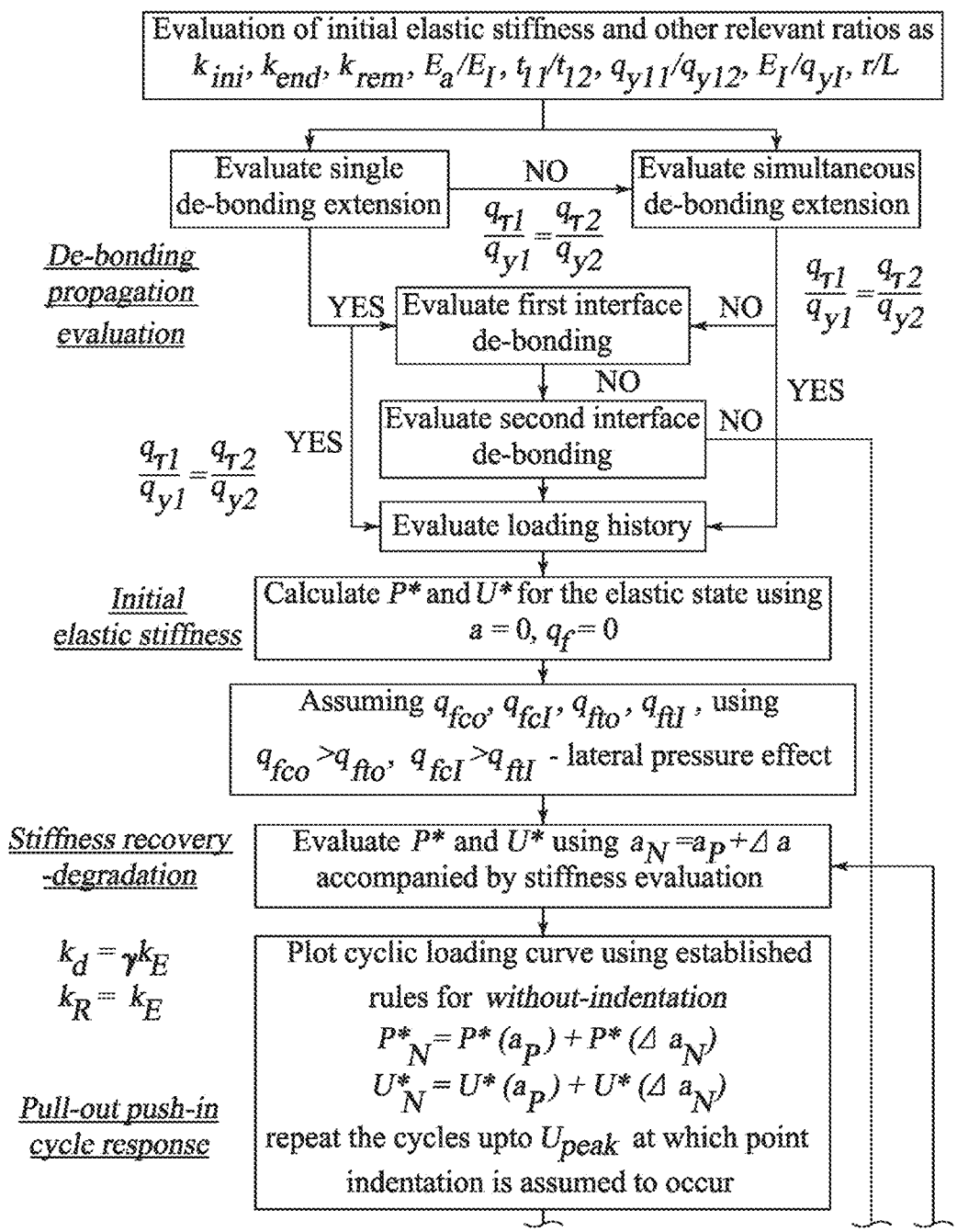
FIG. 14A is an exemplary flowchart of steps employed in the sample calculations of the cyclic response factor.
Figure 14B:
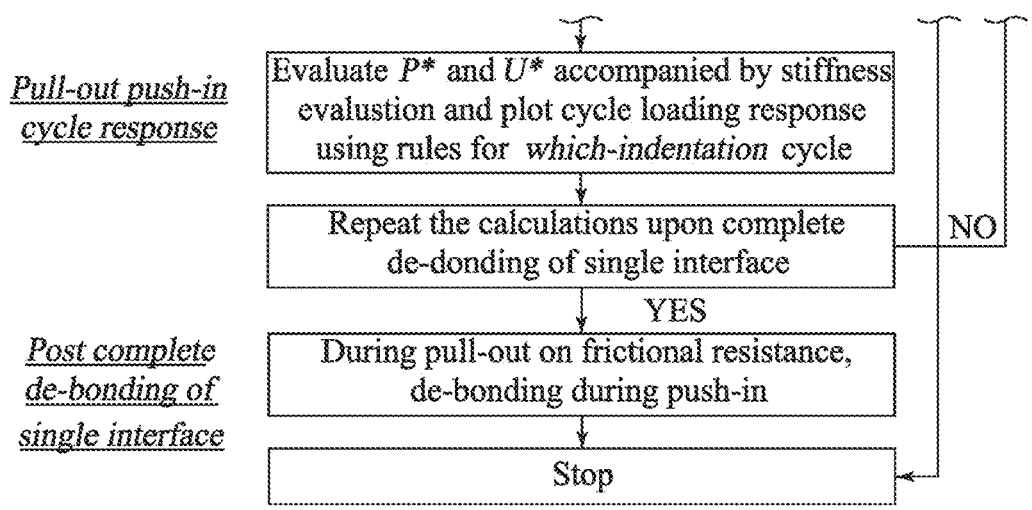
FIG. 14B is a continuation of the exemplary flowchart of steps employed in the sample calculations of the cyclic response factor.

(14) $\quad P_j = -\left(1 - \dfrac{\alpha}{\gamma}\right)P_i$, $U_j = U_i + P_f/k_{dc}$ Using the aforementioned numerical rules, the cyclic pullout push-in response of the post-installed anchor bar can be obtained. FIG. 14A and FIG. 14B show the step-by-step calculation algorithm, which is employed to plot the cyclic response of the post-installed anchor bar. The calculations begin with evaluation of the geometric and material parameters. Once these parameters are finalized, the de-bonding crack extension criterion is evaluated, and based on the satisfaction of crack extension criterion, the interfacial de-bonding is considered. Using the typically employed geometrical parameters, the r/L ratio is taken as 1/40, where r is the radius of the anchor bar taken equal to 19 mm and L is the embedment length taken equal to 20 times diameter of the bar, $d_b$. The elastic modulus ratio of anchor to infill Ea/EI is taken equal to 10, and $E_I/g_{yI}$ is taken equal to 30 where $q_{yI}$ is the yield strength of the infill layer. The typical loading history employed for this purpose has been shown in FIG. 11. The loading history comprises of three parts. The first is pre-indentation part where the negative shear slip is restricted representing the condition of without indentation simulated by the loading cycle abc'cdd'e in FIG. 13A using the rules mentioned in Table 1. The second part of the loading history shows the cycle with indentation shows the cycle with indentation where the negative shear slip is allowed represented by the load cycle zfg'ghi'ijq as shown in FIG. 13A and can be obtained using the rules mentioned from Table 1.

EXAMPLE 4

Cyclic Pull-Out Push-in Response with Finite Element Model

Finite element software ATENA was employed to simulate the cyclic pull-out push-in response of the post-installed anchor bar. 2D interface material model available in the material library of the finite element software was used to represent the piecewise linear material model presented in the above section. The material model uses Mohr-coulomb failure criteria for analysis. Table 1 shows the material properties used in the analysis for representing 2D interface material model, where the subscript c represents the initial closed stiffness of the infill interface before de-bonding representing the condition prior to crack propagation and the subscript o represents the opened stiffness of the infill interface after the propagation of de-bonding representing the deterioration in the stiffness due to de-bonding at the interface. The minimum stiffness after de-bonding propagation is taken equal to 0.001 times the initial maximum stiffness based on software literature recommendation. Table 2 and Table 3 represent the material properties of anchor bar and infill steel cylinders along with the base concrete used for analysis. In case of a piecewise linear material model, the sharp changes in the shape of the model at load reversing points hinder the convergence of solution during the finite element analysis. Therefore, foreseeing the convergence problem associated with implementing the piecewise linear material model in the finite element analysis, two continuous models, namely Menegotto-Pinto material model (1973) and Duncan and Chang material model (1970), also suitable for representing the interface material behavior are also considered. Although these material models are not used to simulate the cyclic pull-out push-in response of the concrete reinforcement anchor in the present results, but the view of the author here for these recommendations is to provide an alternative solution in case of convergence error.

TABLE 2

Material properties of 2D interface

| Material type | 2D interface | |
|---|---|---|
| Normal stiffness ($K_{nn-c}$[≡]) | $2.0 \times 10^4$ | MN/m$^3$ |
| Normal stiffness ($K_{nn-o}$[≡]) | $0.2 \times 10^2$ | MN/m$^3$ |
| Tangential stiffness ($K^{\equiv}$) | $2.0 \times 10^4$ | MN/m$^3$ |
| Tangential stiffness ($K^{\equiv}$) | $0.2 \times 10^2$ | MN/m$^3$ |
| Tensile strength ($f_t$) | $2.0 \times 10^{-1}$ | MPa |
| Cohesion (c) | 1.0 | MPa |
| Friction coefficient ($\varphi$) | 0.1 | — |

[≡]The subscript c stands for closed infill interface and o stands for opened infill interface

TABLE 3

Material properties of steel

| Material type | Bilinear steel von Mises | |
| --- | --- | --- |
| Elastic modulus ($E_s$) | 210 | GPa |
| Poisson's ratio (v) | 0.3 | — |
| Yield strength | 170 | MPa |
| Hardening modulus | 0 | MPa |

TABLE 4

Material properties of concrete

| Material type | SBETA material | |
| --- | --- | --- |
| Elastic modulus ($E_c$) | $3.4 \times 10^4$ | MPa |
| Poisson's ratio (v) | 0.2 | — |
| Compressive strength ($f_c$) | 40 | MPa |
| Tensile strength ($f_t$) | 3.2 | MPa |
| Type of tension softening | Exponential | |
| Crack model | Fixed | |

Figure 15:
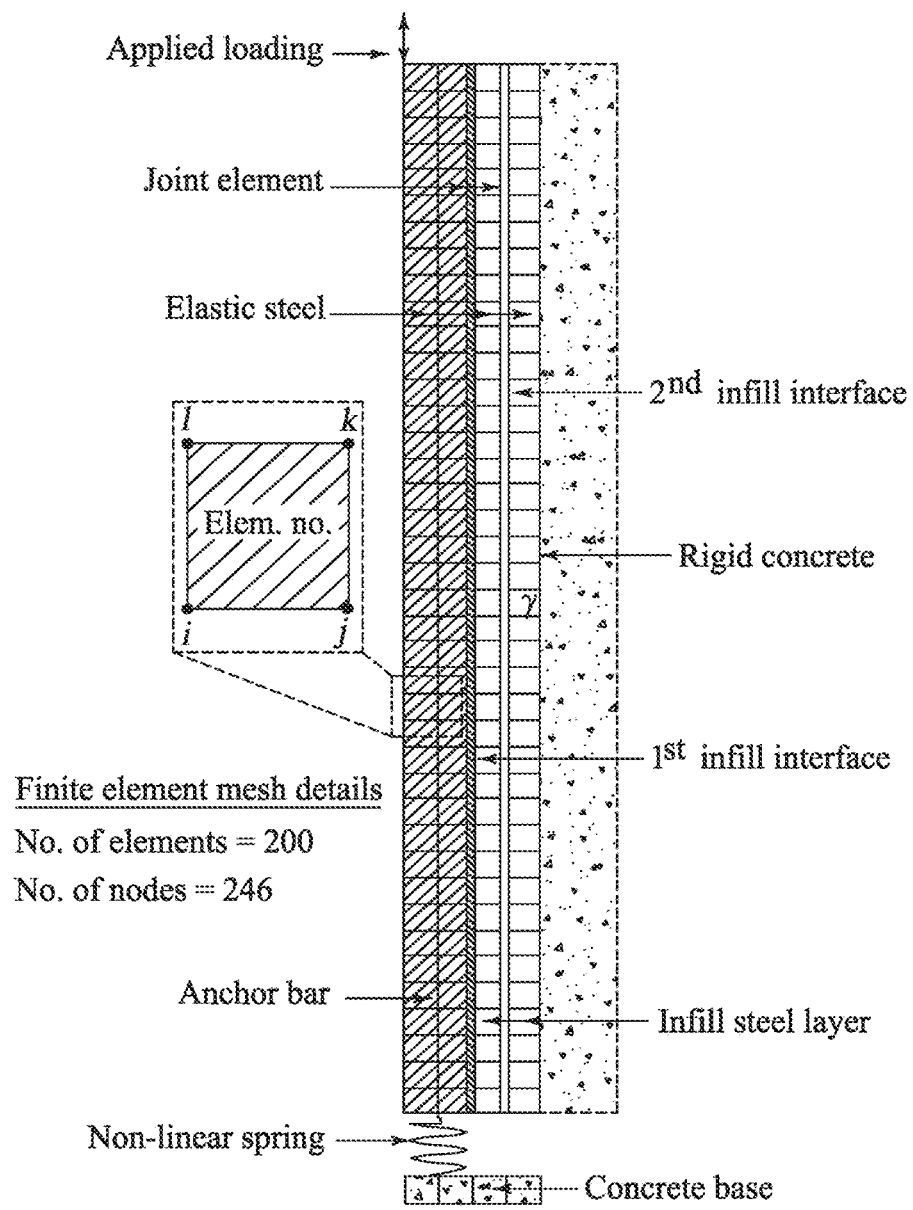
FIG. 15 is a schematic diagram of the model employed in finite element analysis in the sample calculation of the cyclic response factor.

The horizontal part of the anchor-infill assembly was divided into 5 layers while the vertical part was divided into 40 layers as shown in FIG. 15. The anchor bar and the surrounding steel hollow cylinders were modeled using the bilinear von Mises steel material model, and the surrounding concrete was modeled as SBETA material model used to represent concrete in the finite element software (see Table 3 and Table 4). The nonlinear deformable infill layers were modeled as a joint element between two layers using 2D interface material model. Four-node quadrilateral elements were used for the analysis with unit displacement prescribed at the top of the anchor bar to simulate the pull-out push-in applied loading history. The loading history used for getting the cyclic response of the post-installed anchor bar has been described in the previous section and is shown in FIG. 11. A nonlinear spring was attached at the bottom of the anchor bar to represent the opening and closing of space available at the base of the anchor bar. The spring was active under push-in while it was inactive during the pull-out loading cycle offering no resistance. One end of the spring was fixed to simulate the bottom of the hole representing the condition when the anchor bar comes in contact with the base of the drilled hole. All the possibilities related to the support condition of the anchor bar were taken into considerations. These were divided into three cases, namely no resistance shown by the abbreviation NR representing the condition when the concrete at the base of the anchor hole is very weak and does not offer any resistance at all and also the case when the hole in which the anchor bar is fixed is larger than the anchor bar length, and hence, the anchor bar never touches the base of the hole and is allowed to oscillate freely. The second condition is when there is no indentation at the bottom of the hole shown by the abbreviation NI, representing the condition when the concrete at the bottom of the anchor hole is strong enough to support the load without crushing under push-in loading cycle and the final support condition is the case with partial support of the anchor bar abbreviated by WI, showing the condition when the concrete at the base of the anchor hole crushes a little under the action of applied loading but does offer resistance to crushing and is able to resist further crushing under the application of push-in loading. All these conditions were modeled individually, and the response of the anchor bar subjected to these conditions is presented in the proceeding section.

EXAMPLE 5

Response for Pull-Out Push-in Loading

Figure 16A:
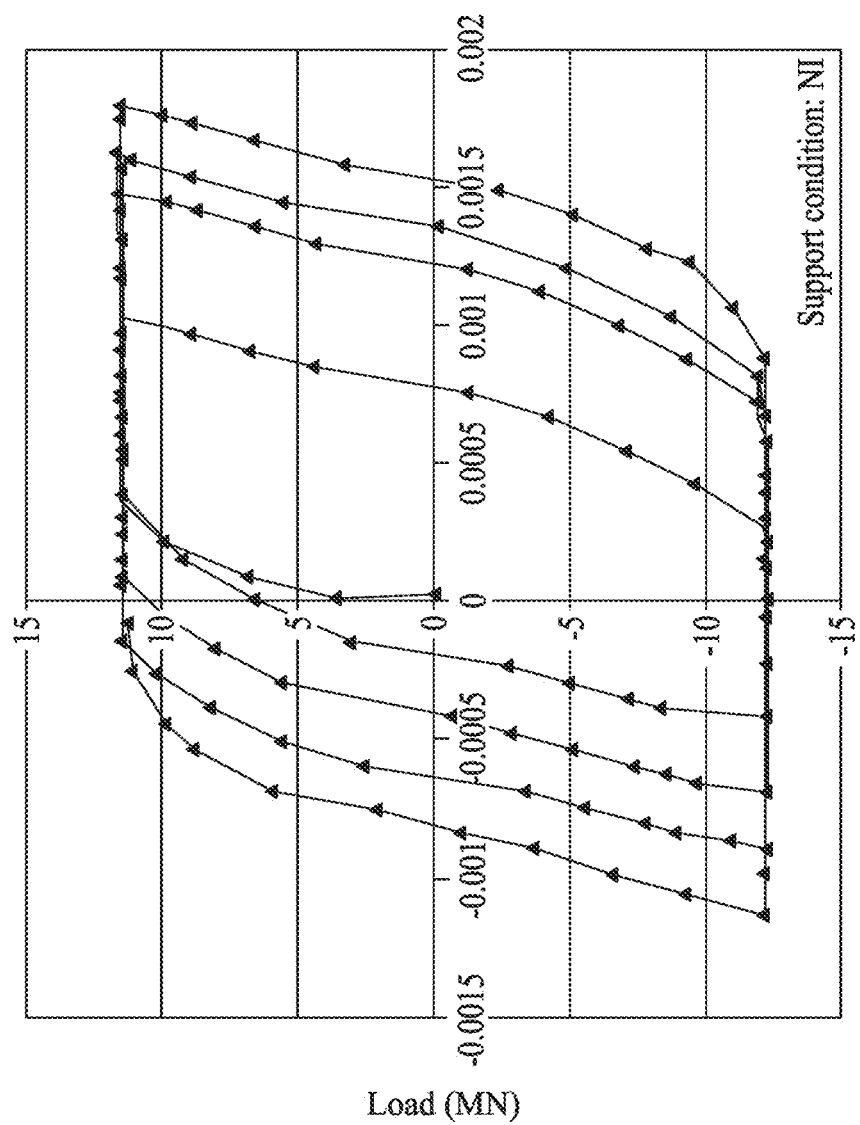
FIG. 16A is an exemplary diagram of the cyclic response curve as a result of the finite element analysis.

FIG. 16A shows the cyclic pull-out push-in response of the post-installed anchor bar under the no resistance (NR) condition when the concrete at the bottom of the anchor hole does not offer any resistance at all and the anchor bar is freely allowed to displace under the push-in loading cycle. The horizontal axis represents the displacements in m, while the vertical axis depicts the pull-out push-in loading MN. It can be seen that initially the load-displacement curve starts with the elastic loading stage S1, followed by pull-out de-bonding stage S2. After that, the pull-out loading is removed and the load-displacement curve begins to reverse as demonstrated earlier by stage S3. Then, the partial recovery of stiffness takes place during the push-in loading cycle given stage S4, and now, since in this case the post-installed anchor bar does not comes in contact with the base of the drilled hole, so there is no resistance offered by the base concrete against the negative displacements and the anchor bar continues the negative displacements without increase in the push-in loading (S5) till the push-in load finally reverses and pull-out cycle begins given by stage S6. The only resistance offered during the push-in loading cycle is the frictional resistive shear force acting on the de-bonded interface.

Figure 16B:
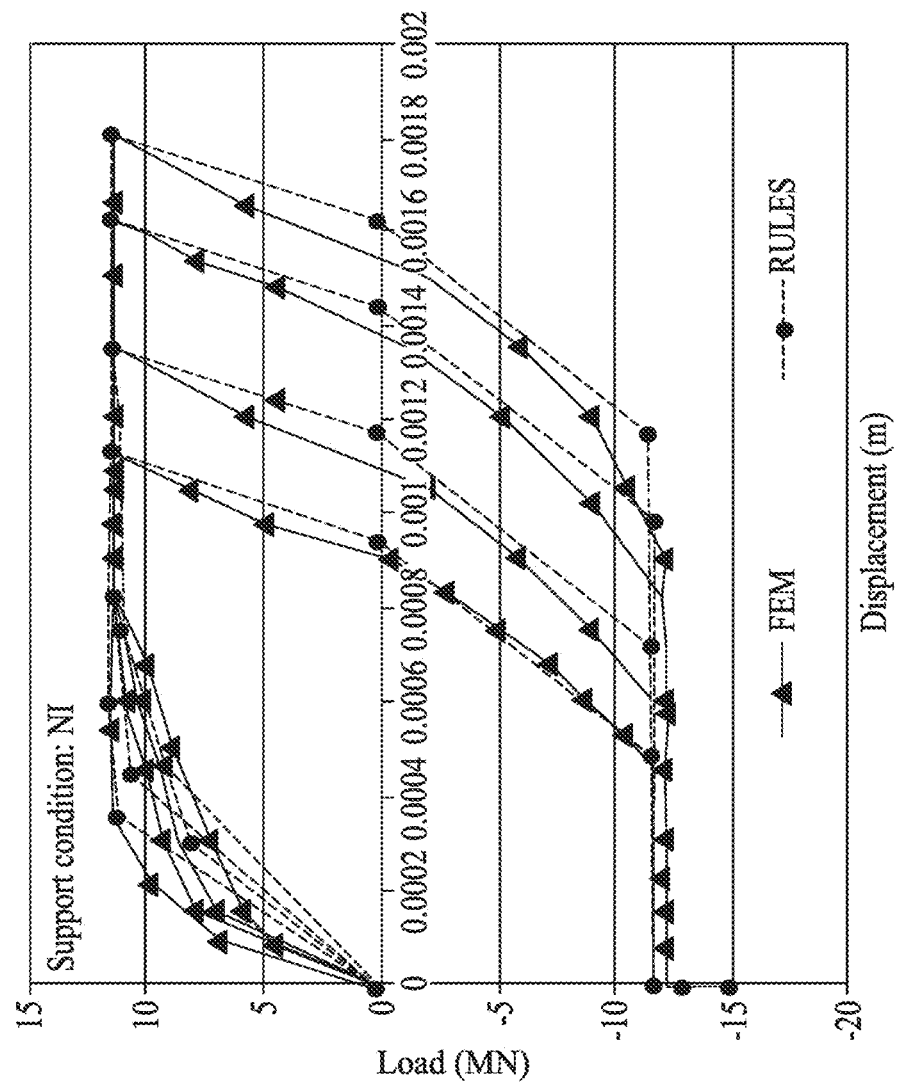
FIG. 16B is an exemplary diagram of the cyclic response curve as a result of the finite element analysis with no indentation as a variable.

FIG. 16B depicts the response of the anchor bar under the condition of no indentation (NI) representing the situation when the concrete at the bottom of the anchor hole is strong enough, so that it does not crush under the application of applied loading, hence resulting in no negative displacements. This was achieved in the finite element analysis by modeling a rigid concrete element at the base of the anchor bar which is modeled with fixed support condition, so that when the anchor bar comes in contact with the base, then there is no further displacement.

Figure 17A:
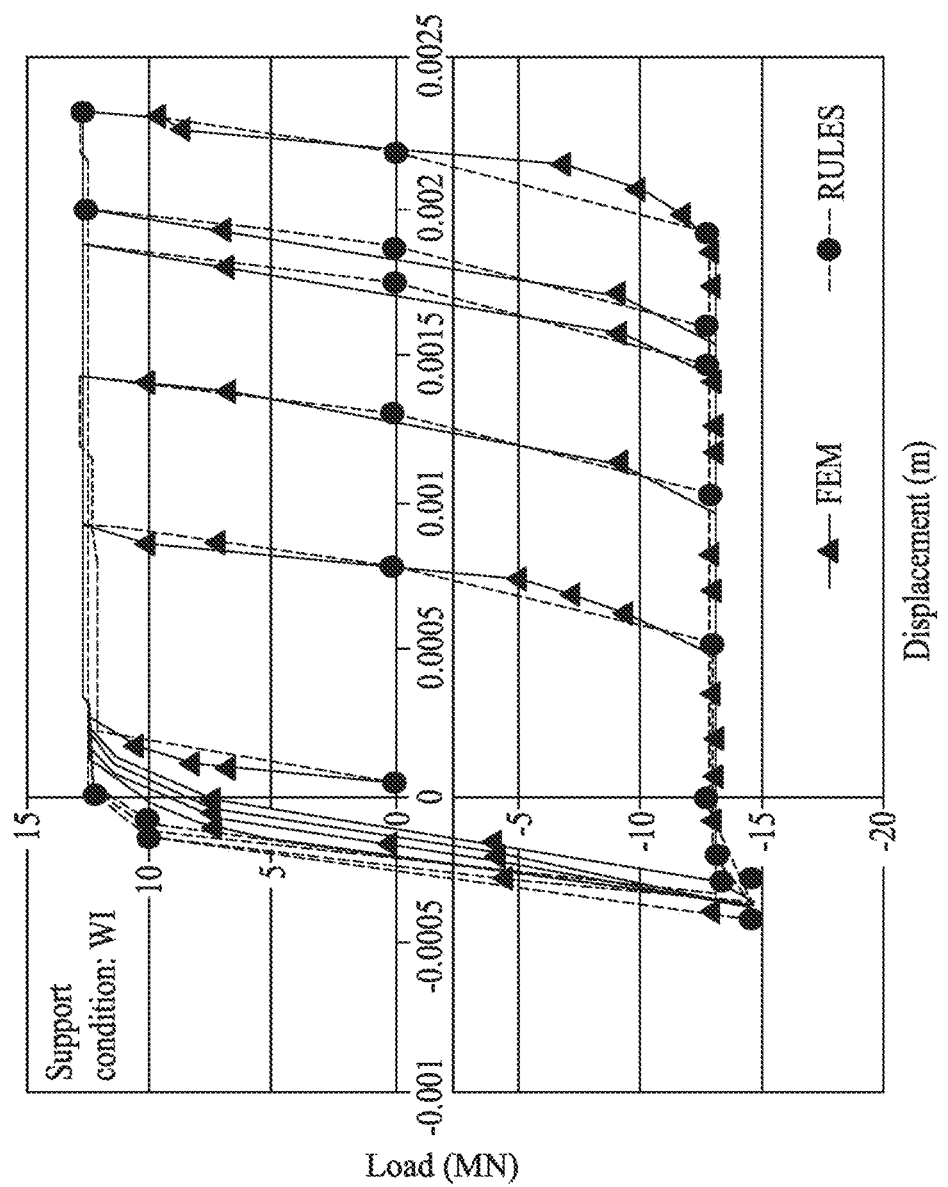
FIG. 17A an exemplary diagram of the cyclic response curve resulting from the finite element analysis with indentation as a variable.

FIG. 17A represents the response of the post-installed anchor bar under the condition with indentation. This condition represents the situation when some concrete at the base of the anchor hole has crushed. This is achieved by modeling a rigid concrete element at the base of the anchor bar and connecting the two together at the interface of the two macroelements with the help of a nonlinear spring described earlier, which is active under compression (push-in) but offers no resistance in tension (pull-out). It can be seen in FIG. 17A that as the anchor bar comes in contact with the base of the anchor hole, some displacements are allowed but once it touches the firm base and the displacements are restricted, the load continues to increase before reversing but the displacements are restricted representing a small amount of concrete crushing at the base of the anchor hole. Indentation is assumed to be 15% of $U_{peak}$ in the present simulation.

Comparisons are made between the cyclic responses predicted by the numerical approach using the finite element method and the analytical rules presented earlier. The results of these comparisons are shown in FIG. 16B and FIG. 17A and it is seen that a good agreement is found between the analytical and numerical approaches, and hence, it can be concluded that the proposed analytical rules can be used to get the cyclic response factor of the concrete reinforcement assembly. During the analysis, it was seen that initially a single interface starts to de-bond accompanied with slight de-bonding at the adjacent interface; afterward, the single-interface de-bond propagates and reaches the bottom of the anchor bar, and here onward, the adjacent infill interface becomes active during the push-in loading cycle and starts to provide a larger failure path and sustains loading during the push-in cycle. However, at this stage, during the pull-out loading cycle, the only resistance offered by the infill interface is the frictional shear resistance, thereby proving the effectiveness of the two-layer model in providing a larger failure path length and energy absorption as presented in the proceeding section.

EXAMPLE 6

Two-Layer Anchor-Infill Assembly: Effectiveness

Figure 17B:
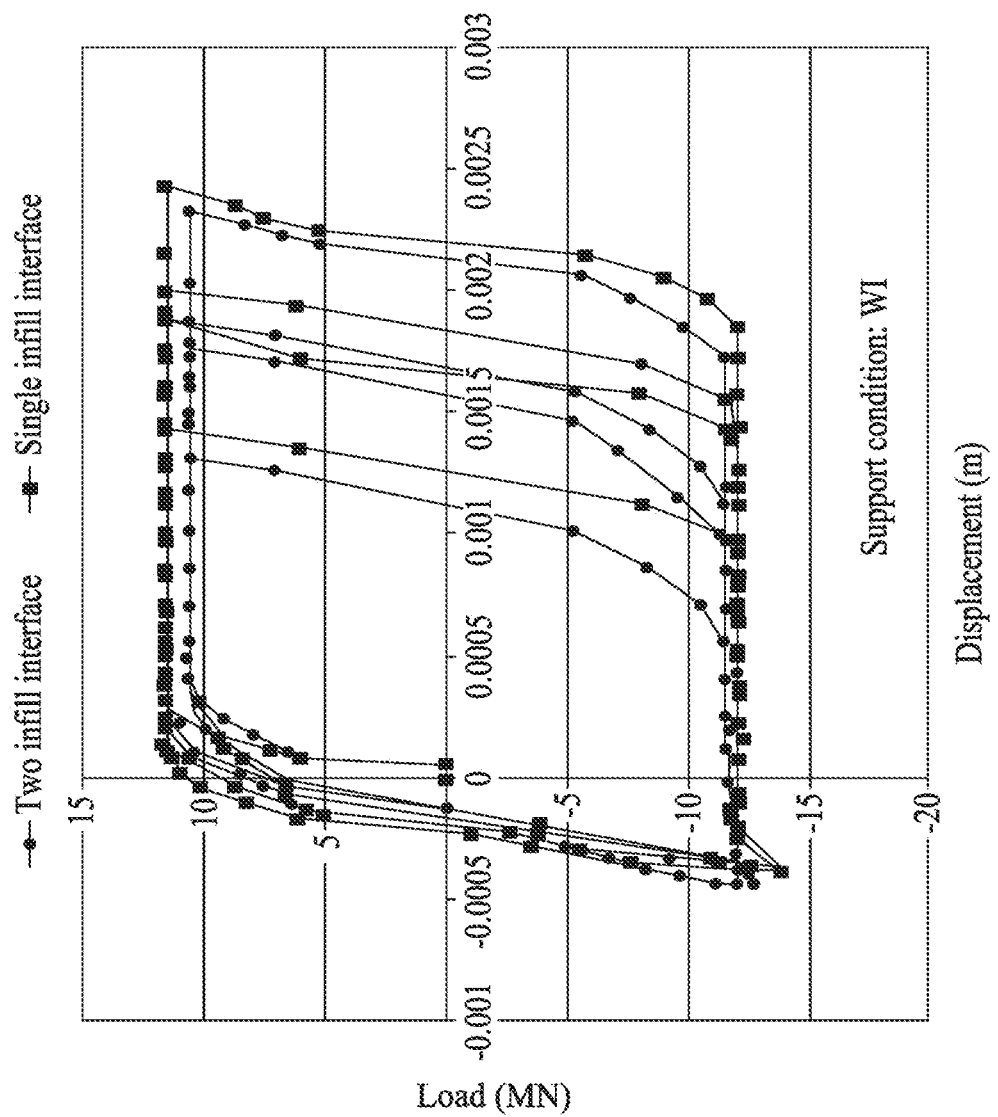
FIG. 17B an exemplary diagram of two cyclic response curves with the concrete reinforcement assembly with two hollow metal sleeves and one hollow metal sleeve.
Figure 18:
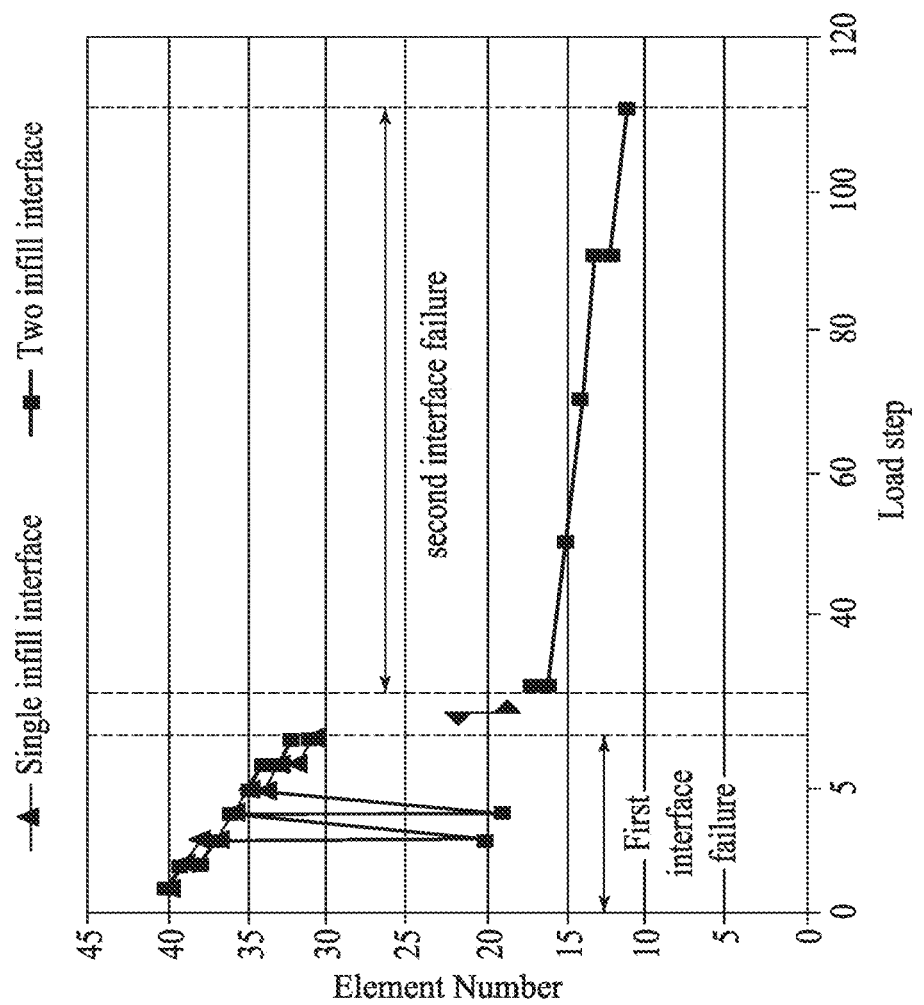
FIG. 18 an exemplary diagram of the cyclic response curve during failure of the concrete reinforcement assembly.

The following section describes the effectiveness of the proposed two-layer anchor-infill assembly as verified by coin paring its cyclic pull-out push-in response with that of the single infill interface model as shown in FIG. 17B. As mentioned earlier, the purpose of dividing the infill material into two layers is to provide a larger failure path, which results in larger energy consumption during the cyclic response of the concrete reinforcement assembly. FIG. 17B shows the comparison of the cyclic pull-out push-in response of the two-interface model and the single-interface model, and FIG. 18 depicts the failure path development sequence for both models. It can be seen in FIG. 17B that the cyclic pull-out push-in response curve of the two-layer model surrounds the curve of single interface model. Same loading history as shown in FIG. 17A was adopted for getting the cyclic response. The anchor infill assembly was divided into five horizontal layers for two-interface model and three horizontal layers for single interface model, and in both cases, the vertical part of the anchor-infill assembly was divided into 40 layers as shown in FIG. 15. The material properties of the infill interface are shown in Table 2 and that of anchor bar, infill steel case and surrounding concrete are shown in Table 3 and Table 4 respectively. The cyclic response is plotted for the support condition of with indentation (WI) as in this case after the complete de-bonding of the single infill interface, the adjacent interface which is dormant up to this stage becomes effective during the push-in loading cycle and results in providing a larger failure path length helping in absorbing extra energy as shown in FIG. 17B. In FIG. 18, it can be seen that for the case of single infill interface model the complete de-bonding occurs during the pull-out loading cycle and during the push-in loading cycle the only resistance offered is the frictional shear resistance where as for the case of two infill interface model after the complete de-bonding of the first interface during the pullout cycle, during the push-in loading cycle when the anchor bar comes in contact with the concrete at the base of anchor hole, the second infill interface starts to de-bond providing a larger failure path length and absorbing extra energy, where the energy consumed corresponds to the area underneath the curve.

As shown in FIG. 17B in both cases, the loading cycle initially begins with elastic load stage S1 followed by de-bonding in the pull-out direction (S2), and this leads to unloading (S3) and reloading stages (S4). At this point in the single infill interface model since the interface has completely de-bonded so during the push-in cycle, the only resistance offered is the frictional shear resistance (S5) followed by unloading of the push-in cycle (S6). However, in the case of two infill interface model at this stage, once the anchor bar comes in contact with the concrete at the base of the concrete hole, the second infill interface starts to de-bond and becomes effective. This results in increasing the failure path length by 80% and increase in energy absorption capacity by 24%. The pull-out load also increases by 16% but this phenomenon is mainly associated with the simultaneous crack extension.

The invention claimed is:

1. A concrete reinforcement assembly comprising:
a first hollow metal sleeve having two ends;
an anchor bar that is nested concentrically within the first hollow metal sleeve and is moveable along a longitudinal axis of the first hollow metal sleeve;
a second hollow metal sleeve having two ends, wherein the first hollow metal sleeve is nested concentrically within the second hollow metal sleeve; and
an infill material, wherein the infill material is disposed in between the first hollow metal sleeve and the anchor bar, and in between the first hollow metal sleeve and the second hollow metal sleeve and cured to dampen energy transfer to and from the concrete reinforcement assembly;
wherein the concrete reinforcement assembly is inserted into a hollow cavity in a concrete structure and adapted to structurally reinforce the concrete structure.

2. The concrete reinforcement assembly of claim 1, further comprising a plurality of mechanical anchors attached to an outer surface of the second hollow metal sleeve adapted to secure the concrete reinforcement assembly to the hollow cavity in the concrete structure by opening outwardly from the outer surface.

3. The concrete reinforcement assembly of claim 2, wherein the mechanical anchors are attached to the outer surface of the second hollow metal sleeve by a hinge and the mechanical anchors can adopt an open position or closed position, where the mechanical anchors extend outwardly when in the open position.

4. The concrete reinforcement assembly of claim 3, wherein the mechanical anchors are in an open position when the anchor bar is within the concrete reinforcement assembly.

5. The concrete reinforcement assembly of claim 2, wherein the mechanical anchors comprise steel.

6. The concrete reinforcement assembly of claim 2, wherein the mechanical anchors are attached to the outer surface of the second hollow metal sleeve at a variety of horizontally and vertically separated levels.

7. The concrete reinforcement assembly of claim 1, wherein the infill material comprises at least one reinforcing material selected from the group consisting of an elastomeric polymer, a glass fiber epoxy composite, a carbon nanotube epoxy composite, and an epoxy, and at least one anti-corrosive additive selected from the group consisting of a polythiophene, calcium sulfonate, barium sulfonate, and an amine.

8. The concrete reinforcement assembly of claim 1, wherein an elastic modulus ratio of the anchor bar to the infill material is 8-25.

9. The concrete reinforcement assembly of claim 1, wherein the first hollow metal sleeve, second hollow metal sleeve, and the anchor bar comprise carbon steel or alloy steel.

10. The concrete reinforcement assembly of claim 1, wherein a longitudinal length of the first hollow metal sleeve and the second hollow metal sleeve is the same as a longitudinal length of the hollow cavity.

11. The concrete reinforcement assembly of claim 1, wherein a ratio of a longest cross sectional length of the anchor bar to a longitudinal length of the hollow cavity ranges from 1:20-1:50.

12. The concrete reinforcement assembly of claim 1, wherein the anchor bar is at least 5%-50% longer in length than the hollow cavity.

13. The concrete reinforcement assembly of claim 1, wherein a cross section of the anchor bar has a shape similar to a cross section of the first hollow metal sleeve.

14. The concrete reinforcement assembly of claim 1, wherein the anchor bar, the first hollow metal sleeve and the second hollow metal sleeve are cylindrical.

15. A method for repairing a damaged concrete anchor comprising:
- removing the damaged concrete anchor from a hollow cavity in a concrete structure;
- inserting a concrete reinforcement assembly comprising a first hollow metal sleeve and a second hollow metal sleeve with an outer surface, wherein the first hollow metal sleeve is nested concentrically within the second hollow metal sleeve, and the outer surface of the second hollow metal sleeve is attached by a plurality of hinges to a plurality of mechanical anchors that are adapted to secure the concrete reinforcement assembly to the hollow cavity in the concrete structure;
- disposing an infill material in between the first hollow metal sleeve and the second hollow metal sleeve;
- inserting an anchor bar concentrically within the first hollow metal sleeve such that the anchor bar is moveable along a longitudinal axis of the first hollow metal sleeve; and
- disposing the infill material in between the first hollow metal sleeve and the anchor bar.

16. The method of claim 15, further comprising resurfacing the hollow cavity in the concrete structure after removing the damaged concrete anchor.

17. The method of claim 15, wherein the insertion of the anchor bar triggers a plurality of mechanical anchors to open.

18. A non-transitory computer readable medium having stored thereon a program that, when executed by a computer, causes the computer to execute a method of determining a cyclic response factor of a concrete reinforcement assembly in a concrete structure comprising:
- receiving a plurality of parameters of the concrete reinforcement assembly and evaluating the plurality of parameters of the concrete reinforcement assembly;
- evaluating a de-bonding extension criterion;
- evaluating a first interfacial de-bonding value based on the plurality of parameters of the concrete reinforcement assembly;
- determining a shear stress parameter and a shear slip parameter and determining a plurality of frictional shear stress parameters;
- estimating a shear stress factor, a shear slip factor, and a stiffness factor;
- establishing a relationship between the plurality of parameters of the concrete reinforcement assembly, the de-bonding extension criterion, the shear stress parameter, the shear slip parameter, and the plurality of frictional shear stress parameters;
- updating the plurality of parameters of the concrete reinforcement assembly; and
- obtaining the cyclic response factor.

19. The method of claim 18, further comprising evaluating a second interfacial de-bonding value based on the plurality of parameters.

20. The method of claim 18, wherein the plurality of parameters includes at least one of a geometrical parameter of the concrete reinforcement assembly, an elastic modulus ratio of the concrete reinforcement assembly, and a loading history of the concrete structure.

* * * * *